(12) United States Patent
Yoshioka et al.

(10) Patent No.: US 9,693,738 B2
(45) Date of Patent: Jul. 4, 2017

(54) HEARTBEAT MEASURING APPARATUS, HEARTBEAT MEASURING METHOD, AND RECORDING MEDIUM

(71) Applicant: Panasonic Corporation, Osaka (JP)

(72) Inventors: Mototaka Yoshioka, Osaka (JP); Takeshi Fukuda, Osaka (JP); Toru Sato, Kyoto (JP); Takuya Sakamoto, Hyogo (JP)

(73) Assignee: PANASONIC CORPORATION, Osaka (JP)

(*) Notice: Subject to any disclaimer, the term of this patent is extended or adjusted under 35 U.S.C. 154(b) by 0 days.

(21) Appl. No.: 15/156,335

(22) Filed: May 17, 2016

(65) Prior Publication Data

US 2016/0338652 A1    Nov. 24, 2016

(30) Foreign Application Priority Data

May 22, 2015  (JP) .................. 2015-104614

(51) Int. Cl.
  *A61B 5/00*    (2006.01)
  *A61B 5/024*   (2006.01)
  *A61B 5/05*    (2006.01)

(52) U.S. Cl.
  CPC ........ *A61B 5/7282* (2013.01); *A61B 5/02444* (2013.01); *A61B 5/0507* (2013.01); *A61B 5/7239* (2013.01)

(58) Field of Classification Search
  None
  See application file for complete search history.

(56) References Cited

U.S. PATENT DOCUMENTS

| 9,241,676 B2 * | 1/2016 | Lisogurski ........... A61B 5/7285 |
| 2009/0015464 A1 | 1/2009 | Fukuda |

FOREIGN PATENT DOCUMENTS

| JP | 8-128871 | 5/1996 |
| JP | 2011-050604 | 3/2011 |
| JP | 2011-107165 | 6/2011 |

* cited by examiner

*Primary Examiner* — Brian T Gedeon
(74) *Attorney, Agent, or Firm* — Wenderoth, Lind & Ponack, L.L.P.

(57) ABSTRACT

A heartbeat measuring apparatus includes a receiver that receives a millimeter wave signal reflected by a user; an identifier that identifies a plurality of characteristic points of the received millimeter wave signal in time series, the characteristic points including a local maximum point, a local minimum point, and an inflection point; a memory that stores a heartbeat characteristic point pattern indicating a first arrangement order of a first inflection point following a first local maximum point, a first local minimum point following the first inflection point, a second inflection point following the first local minimum point, and a second local maximum point following the second inflection point; an acquirer that acquires, from among the identified characteristic points, a first characteristic point set including first characteristic points that are arranged in an order identical to the first arrangement order; and an outputter that outputs heartbeat information on the user.

11 Claims, 25 Drawing Sheets

FIG. 7

| CHARACTERISTIC POINT ID | CHARACTERISTIC SERIES INFORMATION | MARK |
|---|---|---|
| PK (peaks) | $ds(t)/dt = 0$ and $d^2s(t)/dt^2 < 0$ | △ |
| VL (valleys) | $ds(t)/dt = 0$ and $d^2s(t)/dt^2 > 0$ | ▲ |
| RDP (rising derivative peak) | $ds(t)/dt > 0$, $d^2s(t)/dt^2 = 0$ and $d^3s(t)/dt^3 < 0$ | ○ |
| RDV (rising derivative valley) | $ds(t)/dt > 0$, $d^2s(t)/dt^2 = 0$ and $d^3s(t)/dt^3 > 0$ | ● |
| FDP (falling derivative peak) | $ds(t)/dt < 0$, $d^2s(t)/dt^2 = 0$ and $d^3s(t)/dt^3 < 0$ | ■ |
| FDV (falling derivative valley) | $ds(t)/dt < 0$, $d^2s(t)/dt^2 = 0$ and $d^3s(t)/dt^3 > 0$ | □ |

HEARTBEAT MEASURING APPARATUS, HEARTBEAT MEASURING METHOD, AND RECORDING MEDIUM

BACKGROUND

1. Technical Field

The present disclosure relates to a heartbeat measuring apparatus, a heartbeat measuring method, and a recording medium.

2. Description of the Related Art

Japanese Patent No. 5467395 discloses a technique for detecting heartbeats by using electric waves including microwaves reflected by a subject.

SUMMARY

In the related art disclosed in Japanese Patent No. 5467395, however, heartbeats of a subject are measured by performing frequency analysis on reflected waves under the assumption that the reflected waves are synthesized sine waves, and therefore detecting correct heartbeat timings is difficult.

One non-limiting and exemplary embodiment provides a technique for detecting correct heartbeat timings.

In one general aspect, the techniques disclosed here feature a heartbeat measuring apparatus including a receiver that receives a millimeter wave signal reflected by a user; an identifier that identifies a plurality of characteristic points of the received millimeter wave signal in time series, the plurality of characteristic points including a local maximum point, a local minimum point, and an inflection point defined by information representing a positive or negative sign of a slope of the millimeter wave signal and information representing a positive or negative sign of a third-order derivative of the millimeter wave signal; a memory that stores a heartbeat characteristic point pattern indicating a first arrangement order of a first inflection point following a first local maximum point and having a negative slope and a positive third-order derivative, a first local minimum point following the first inflection point, a second inflection point following the first local minimum point and having a positive slope and a negative third-order derivative, and a second local maximum point following the second inflection point; an acquirer that acquires, from among the plurality of characteristic points that have been identified, a first characteristic point set including first characteristic points that are arranged in an order identical to the first arrangement order; and an outputter that outputs heartbeat information on the user including a time based on the first characteristic points included in the first characteristic point set that has been acquired.

It should be noted that general or specific embodiments may be implemented as a system, a method, an integrated circuit, a computer program, a computer-readable recording medium, or any selective combination thereof. The computer-readable recording medium includes a nonvolatile recording medium such as a compact disc-read only memory (CD-ROM).

An embodiment of the present disclosure provides a technique for measuring correct heartbeat timings. Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 7 is a table illustrating a specific example of a plurality of characteristic points of a heartbeat included in a heartbeat characteristic point pattern according to the first embodiment;

DETAILED DESCRIPTION

Underlying Knowledge Forming Basis of the Present Disclosure

Electric waves, including millimeter waves or microwaves, reflected by a chest of a subject include heartbeat information on the subject. However, the electric waves include various pieces of information including noise in addition to the heartbeat information, and thus the signal intensity of the heartbeat information is low.

Heartbeat data (a heartbeat waveform) obtained through the electric waves indicates periodical swings corresponding to heartbeats. In the related art, frequency analysis is performed on the heartbeat waveform to calculate a heart rate, which is an average rate in a certain time period. However, the frequency analysis is based on the assumption that a heartbeat waveform is formed of synthesized sine waves, and thus a local maximum point of heartbeat data may be blunted. In the related art, a heartbeat waveform is filtered and a local maximum value in the heartbeat waveform is extracted to calculate heartbeat timing. However, phase shift resulting from the filtering may cause shift of the position of the local maximum value.

An actual heartbeat waveform is not monotonous repeat of peaks and valleys like sine waves and has a characteristic shape based on heartbeats.

Figure 1:
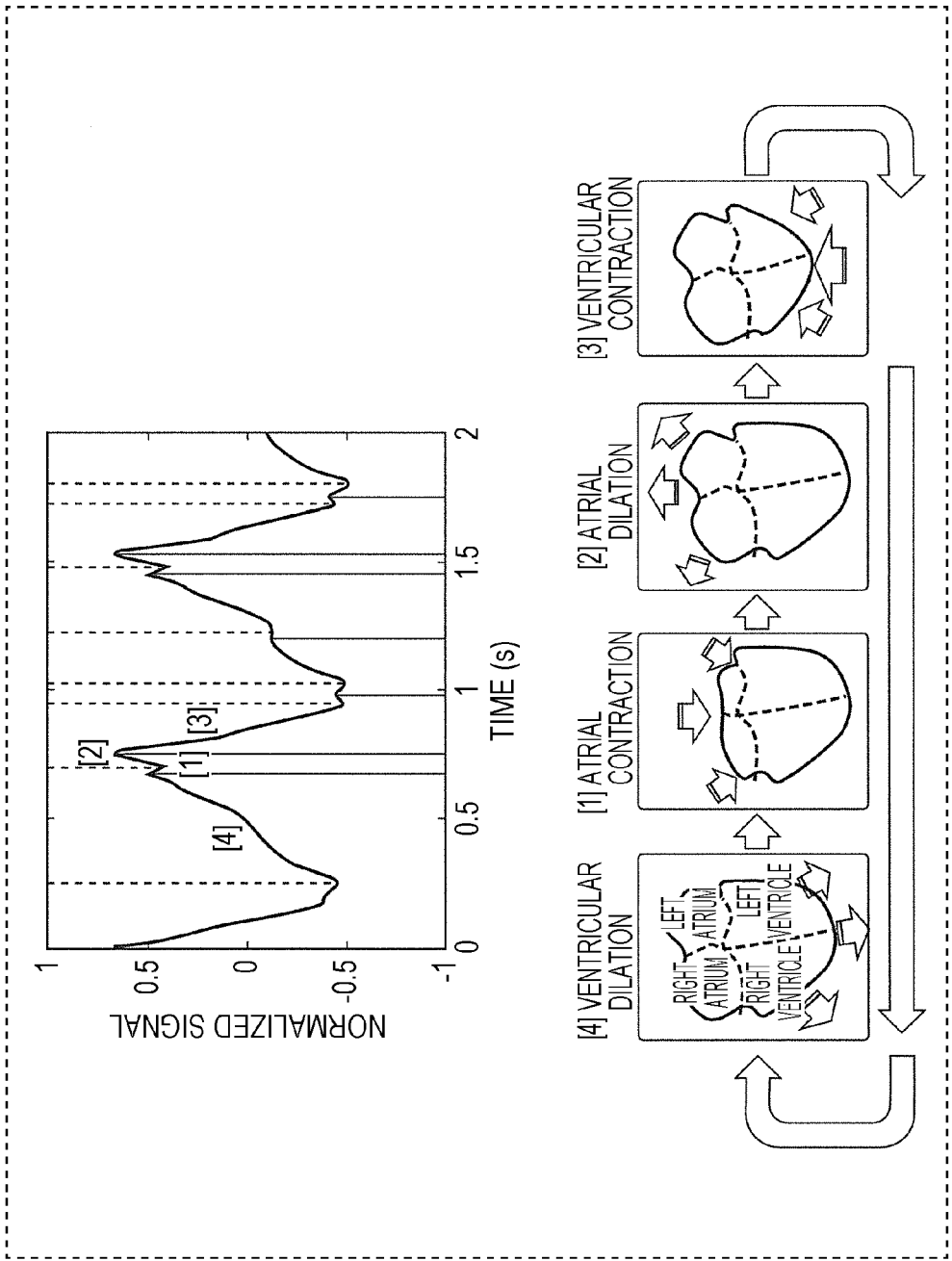
FIG. 1 is a diagram illustrating a relationship between heartbeat data and heartbeats.

FIG. 1 is a diagram illustrating a relationship between heartbeat data and heartbeats.

As illustrated in FIG. 1, the heartbeat data has a shape representing two local maximum points close to each other in one heartbeat. This shape is called a double peak shape, which represents a heartbeat appearing in heartbeat data. The heartbeat includes four movements, as illustrated in FIG. 1. First, the atriums contract as illustrated in [1] of FIG. 1 and then dilate as illustrated in [2] of FIG. 1. Subsequently, the ventricles contract as illustrated in [3] of FIG. 1 and then dilate as illustrated in [4] of FIG. 1. These movements of the heart are represented by the heartbeat data. If typical frequency analysis or filtering is performed on such a heartbeat waveform (heartbeat data) in order to extract two local maximum points, the two local maximum points may be detected as one local maximum point. In addition, phase shift may cause shift of the local maximum point and also large shift of measured timing from actual heartbeat timing.

Accordingly, the inventors have found a heartbeat characteristic point pattern representing heartbeat characteristics. In the present disclosure, heartbeat information can be acquired with high accuracy by using the heartbeat characteristic point pattern.

A heartbeat measuring apparatus according to an aspect of the present disclosure includes a receiver that receives a millimeter wave signal reflected by a user; an identifier that identifies a plurality of characteristic points of the received millimeter wave signal in time series, the plurality of characteristic points including a local maximum point, a local minimum point, and an inflection point defined by information representing a positive or negative sign of a slope of the millimeter wave signal and information representing a positive or negative sign of a third-order derivative of the millimeter wave signal; a memory that stores a heartbeat characteristic point pattern indicating a first arrangement order of a first inflection point following a first local maximum point and having a negative slope and a positive third-order derivative, a first local minimum point following the first inflection point, a second inflection point following the first local minimum point and having a positive slope and a negative third-order derivative, and a second local maximum point following the second inflection point; an acquirer that acquires, from among the plurality of characteristic points that have been identified, a first characteristic point set including first characteristic points that are arranged in an order identical to the first arrangement order; and an outputter that outputs heartbeat information on the user including a time based on the first characteristic points included in the first characteristic point set that has been acquired.

Accordingly, the first characteristic point set corresponding to the heartbeat characteristic point pattern is acquired as a heartbeat, and the time based on the first characteristic points included in the first characteristic point set is measured as a heartbeat timing. Thus, blunting of a local maximum point caused by frequency analysis according to the related art and shift of the position of the local maximum point due to phase shift caused by filtering according to the related art can be suppressed. As a result, correct heartbeat timings can be measured.

The acquirer may further acquire, from among the plurality of characteristic points that have been identified, a second characteristic point set including second characteristic points different from the first characteristic points included in the first characteristic point set, the second characteristic points being arranged in an order identical to the first arrangement order. The outputter may output the heartbeat information on the user further including a time difference which is a difference between a time based on the first characteristic points included in the first characteristic point set and a time based on the second characteristic points included in the second characteristic point set.

Accordingly, heartbeat intervals are output as time differences of correct heartbeat timings, and thus the heartbeat intervals can be correctly measured.

The outputter may search for, among the plurality of characteristic points that have been identified except the first characteristic points included in the first characteristic point set, a plurality of characteristic points whose types are identical to a type of a reference point, the reference point being one of the first characteristic points included in the first characteristic point set. The outputter may determine, based on an intensity of the millimeter wave signal at the reference point and intensities of the millimeter wave signal at the plurality of characteristic points obtained through the search, a corresponding characteristic point that corresponds to the reference point and that is included in a characteristic point set of a heartbeat different from a heartbeat for the first characteristic point set among the plurality of characteristic points whose types are identical to the type of the reference point. The outputter may output the heartbeat information on the user further including a time difference which is a difference between a time of the reference point and a time of the corresponding characteristic point. The type of each of the plurality of characteristic points may be one of a local maximum point, a local minimum point, an inflection point having a negative slope and a positive third-order derivative, an inflection point having a negative slope and a negative third-order derivative, an inflection point having a positive slope and a positive third-order derivative, and an inflection point having a positive slope and a negative third-order derivative.

Accordingly, a heartbeat interval as a time difference can be correctly measured for each of the plurality of characteristic points of the heartbeat for the first characteristic point set. Further, since the plurality of characteristic points whose types are identical to the type of the reference point are searched for and then the corresponding characteristic point is determined based on the signal intensities of the characteristic points, it is not necessary to determine the corresponding characteristic point in consideration of the signal intensities of characteristic points whose types are different from the type of the reference point, and accordingly the amount of calculation can be reduced.

The time difference may be any one of a difference between a time of a first local maximum point included in the first characteristic point set and a time of a first local maximum point included in the second characteristic point set, a difference between a time of a first inflection point included in the first characteristic point set and a time of a first inflection point included in the second characteristic point set, a difference between a time of a local minimum point included in the first characteristic point set and a time of a local minimum point included in the second characteristic point set, a difference between a time of a second inflection point included in the first characteristic point set and a time of a second inflection point included in the second characteristic point set, and a difference between a time of a second local maximum point included in the first characteristic point set and a time of a second local maximum point included in the second characteristic point set.

Hereinafter, embodiments of the present disclosure will be described with reference to the accompanying drawings.

First Embodiment

Figure 2:
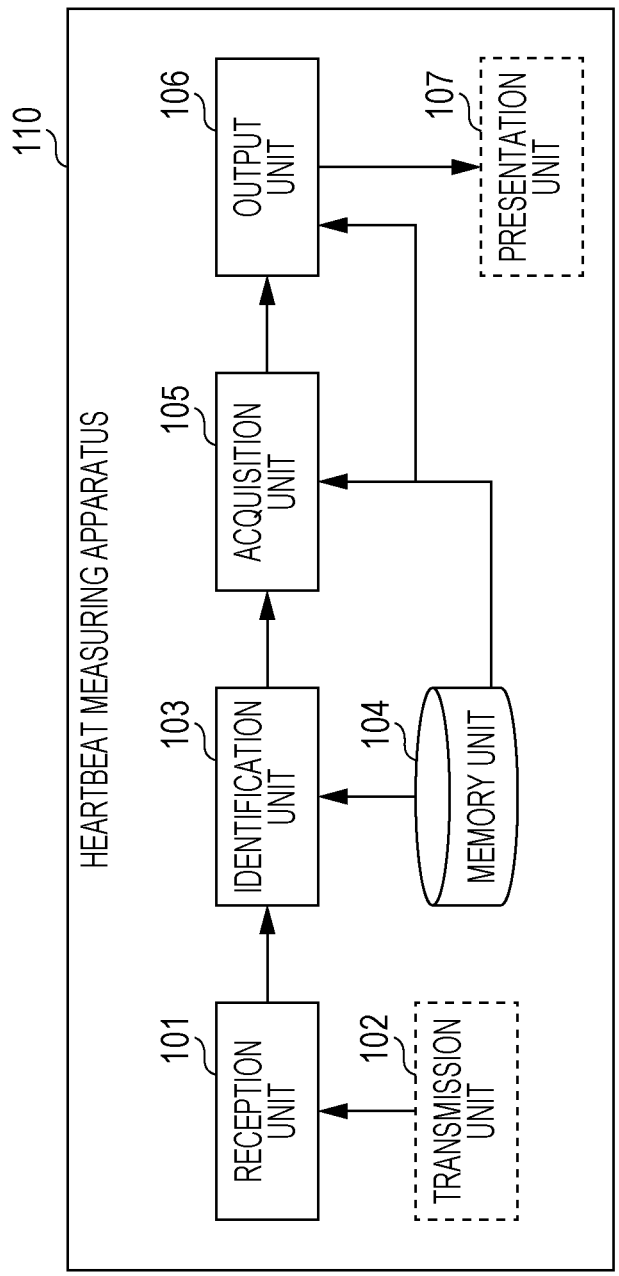
FIG. 2 is a block diagram illustrating the configuration of a heartbeat measuring apparatus according to a first embodiment.

FIG. 2 is a block diagram illustrating the configuration of a heartbeat measuring apparatus 110 according to a first embodiment. As illustrated in FIG. 2, the heartbeat measuring apparatus 110 includes a reception unit 101, a transmission unit 102, an identification unit 103, a memory unit 104, an acquisition unit 105, an output unit 106, and a presentation unit 107.

Figure 3:
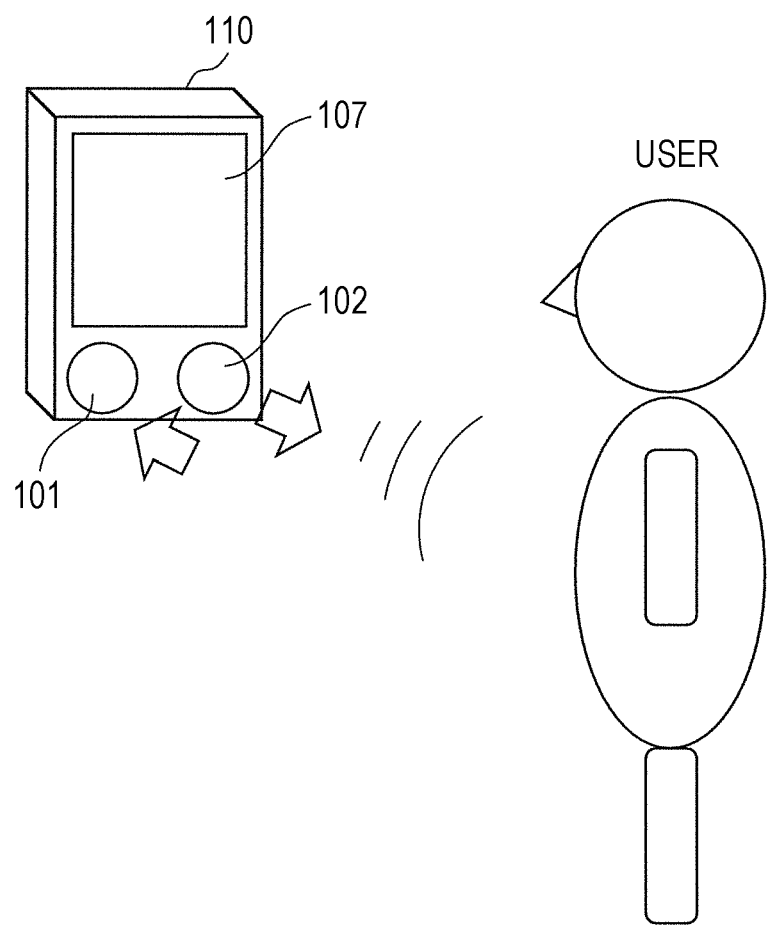
FIG. 3 is a diagram illustrating the outer appearance of the heartbeat measuring apparatus according to the first embodiment.

FIG. 3 illustrates an example of the outer shape of the heartbeat measuring apparatus 110 according to the first embodiment. As illustrated in FIG. 3, the heartbeat measuring apparatus 110 includes functional blocks located in or on a casing. The reception unit 101 and transmission unit 102 for millimeter waves and the presentation unit 107 that presents information are provided on the front surface of the casing of the heartbeat measuring apparatus 110.

The heartbeat measuring apparatus 110 emits millimeter waves from the transmission unit 102 and receives, by the reception unit 101, a millimeter wave signal resulting from the millimeter waves reflected by a person. Accordingly, the heartbeat measuring apparatus 110 detects the person or a movement of the person. In the present disclosure, the heartbeat measuring apparatus 110 detects heartbeats caused by cardiac contraction and dilation, based on a millimeter wave signal reflected by the chest of a person.

Transmission Unit 102

The transmission unit 102 transmits millimeter waves toward the chest of a subject. Examples of the subject include a person who is a user, and a vertebrate animal. The heartbeat measuring apparatus 110 according to the first embodiment does not necessarily include the transmission unit 102. In this case, the reception unit 101 receives a millimeter wave signal resulting from millimeter waves transmitted from an apparatus other than the heartbeat measuring apparatus 110 and reflected by the chest of a subject.

Reception Unit 101

The reception unit 101 receives a millimeter wave signal reflected by a user. Specifically, the reception unit 101 is a control circuit that acquires a millimeter wave signal reflected by the chest of the user as a subject. The reception unit 101 includes a reception antenna that receives a millimeter wave signal reflected by the chest of the subject. The reception unit 101 may receive data of an electric wave signal received by an apparatus other than the heartbeat measuring apparatus 110.

The phase of the millimeter wave signal changes depending on a change in the distance between the subject and the reception unit 101, the change being caused by heartbeats of the subject. The acquired millimeter wave signal includes time series information that depends on the distance between the subject and the reception unit 101. The reception unit 101 may receive electric waves in a frequency band different from that of millimeter waves. A specific example of the electric waves is microwaves.

The reception unit 101 may acquire, based on the millimeter wave signal, information representing at least one of the distance between the subject and the reception unit 101, the phase of the millimeter wave signal, and the signal intensity of the millimeter wave signal. The distance, phase, and signal intensity may be associated with time. The time may be a time as a time point or a time period elapsed from a certain starting point.

The reception unit 101 detects the distance between the subject and the reception unit 101, based on a time difference between a time when the transmission unit 102 transmits millimeter waves and a time when the reception antenna or another apparatus receives a reflected millimeter wave signal. The reception unit 101 may calculate a phase difference or frequency difference by using the millimeter waves transmitted by the transmission unit 102 and information acquired by performing orthogonal detection on the received millimeter wave signal, and may detect a movement of the subject or acquire a movement velocity of the subject.

The reception unit 101 may include a plurality of reception antennas and may detect, based on differences in time when millimeter waves reach each reception antenna, the direction of the subject relative to the reception unit 101 or the distance from the reception unit 101 to the subject.

Regarding the reception of the millimeter wave signal by the reception unit 101 and the calculation of the distance, phase, and signal intensity by the reception unit 101, Japanese Patent No. 5198603 is to be referred to.

Figure 4:
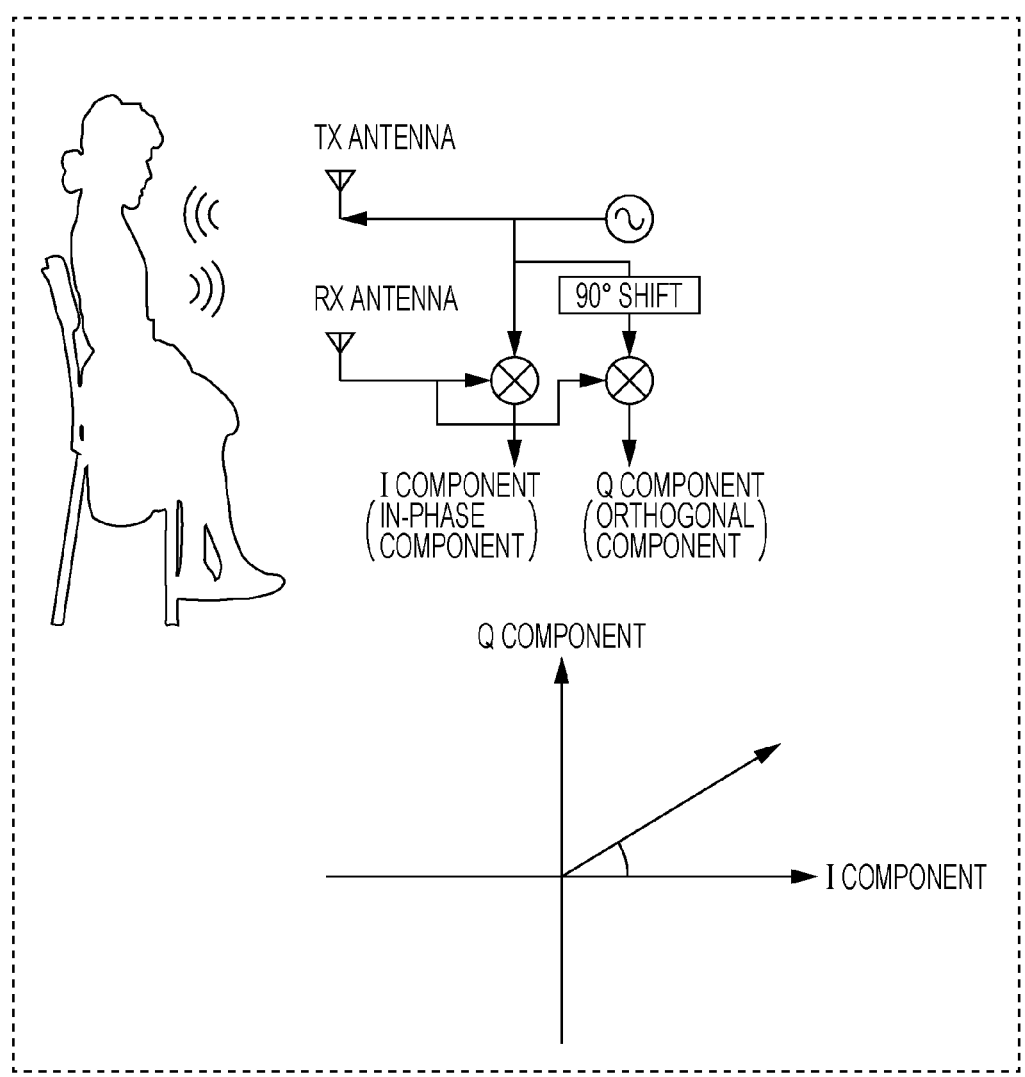
FIG. 4 is an explanatory diagram illustrating the principle of calculation of heartbeat timings according to the first embodiment.

FIG. 4 is an explanatory diagram illustrating the principle of calculating heartbeat timings according to the first embodiment.

The transmission unit 102 transmits a signal or transmission waves as pulse waves (for example, millimeter waves) having a certain frequency. The reception unit 101 receives a signal reflected by the chest of a subject. The transmission signal transmitted as transmission waves may be modulated by using a frequency, amplitude, phase, or sign. The transmission signal may include information representing the time when the transmission unit 102 transmits the transmission signal.

If the reception unit 101 includes a plurality of reception antennas, the distance between the reception unit 101 and the subject can be measured by using differences in arrival time of a millimeter wave signal at the individual reception antennas.

A change in body movements at the chest caused by cardiac contraction or heartbeats can be detected by using a millimeter wave signal reflected by the chest of the person. Since body movements including heartbeats or breathing are very small, a change in distance may be detected by using a difference in arrival time and a phase difference of a millimeter wave signal. The distance d between the subject and the reception unit 101 is calculated by using the following Equations (1) to (5), in which r(t) represents a received millimeter wave signal, c represents a light velocity, and f represents a wavelength.

$$r(t)=A(t)\cos(2\pi f_0(t-2d/c)) \quad \text{Equation (1)}$$

An in-phase component (I) and an orthogonal component (Q) of this signal are respectively expressed by Equations (2) and (3), and the phase of the signal is calculated by using Equation (4).

$$I(t)=A(t)\cos(4\pi f_0 d/c) \quad \text{Equation (2)}$$

$$Q(t)=A(t)\sin(4\pi f_0 d/c) \quad \text{Equation (3)}$$

$$\text{phase}=(4\pi f_0 d/c)=\tan^{-1}(Q/I) \quad \text{Equation (4)}$$

The distance d is calculated by using Equation (5). If a change in phase is large, an unwrapping process may be performed.

$$d=c/4\pi f_0 \tan^{-1}(Q/I) \quad \text{Equation (5)}$$

Figure 5:
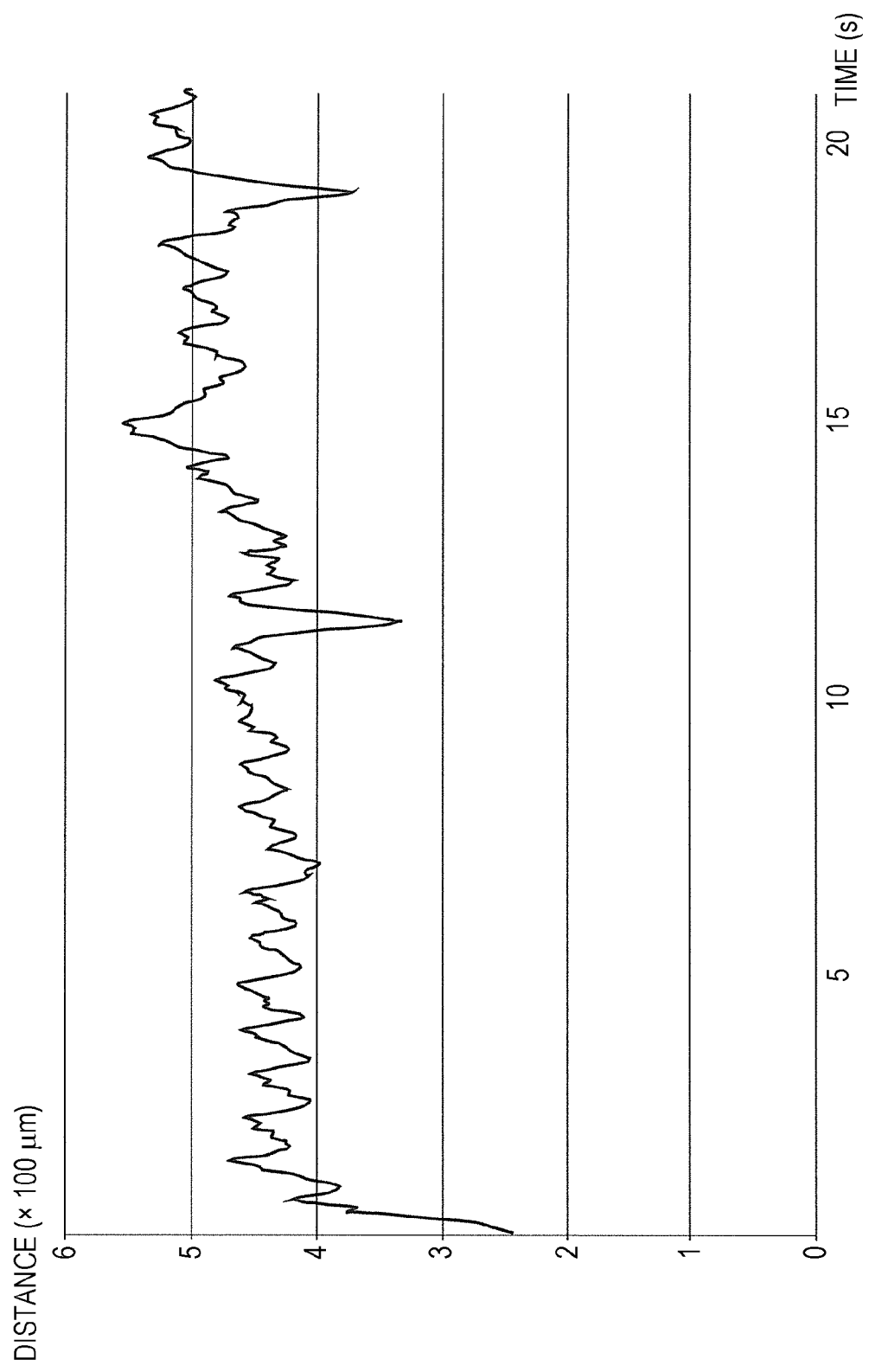
FIG. 5 is a graph illustrating an example of a millimeter wave signal according to the first embodiment.

FIG. 5 illustrates an example of a millimeter wave signal received by the reception unit 101 according to the first embodiment. Hereinafter, the millimeter wave signal received by the reception unit 101 will be referred to as a millimeter wave signal or heartbeat data. The millimeter wave signal illustrated in FIG. 5 is measured by using, as the reception unit 101, a spread spectrum radar using a 26 GHz band.

In FIG. 5, the vertical axis represents the distance (phase difference) between the subject and the reception unit 101 whereas the horizontal axis represents time. A change in the distance between the subject and the reception unit 101 corresponds to a change in movements of the chest of the subject. That is, a change in the millimeter wave signal includes information about movements of the subject heart. The heartbeat data may be expressed by removing trend from the received millimeter wave signal and using a normalized value.

The spread spectrum radar is able to freely set the relationship between a distance resolution and a maximum detection distance by adjusting the chip rate of a PN code and a code cycle. For example, a small change at the chest can be detected by setting the chest within the range.

Identification Unit 103

The identification unit 103 identifies a plurality of characteristic points of a millimeter wave signal in time series, the plurality of characteristic points including a local maximum point, a local minimum point, and an inflection point associated with information representing a positive or negative sign of a slope of the millimeter wave signal and information representing a positive or negative sign of a third-order derivative of the millimeter wave signal. When identifying the plurality of characteristic points, the identification unit 103 refers to characteristic series information, which will be described below with reference to FIG. 7, stored in the memory unit 104. A local maximum point may be a point indicating a local maximum value of a peak, and a local minimum point may be a point indicating a local minimum value of a valley.

Figure 6:
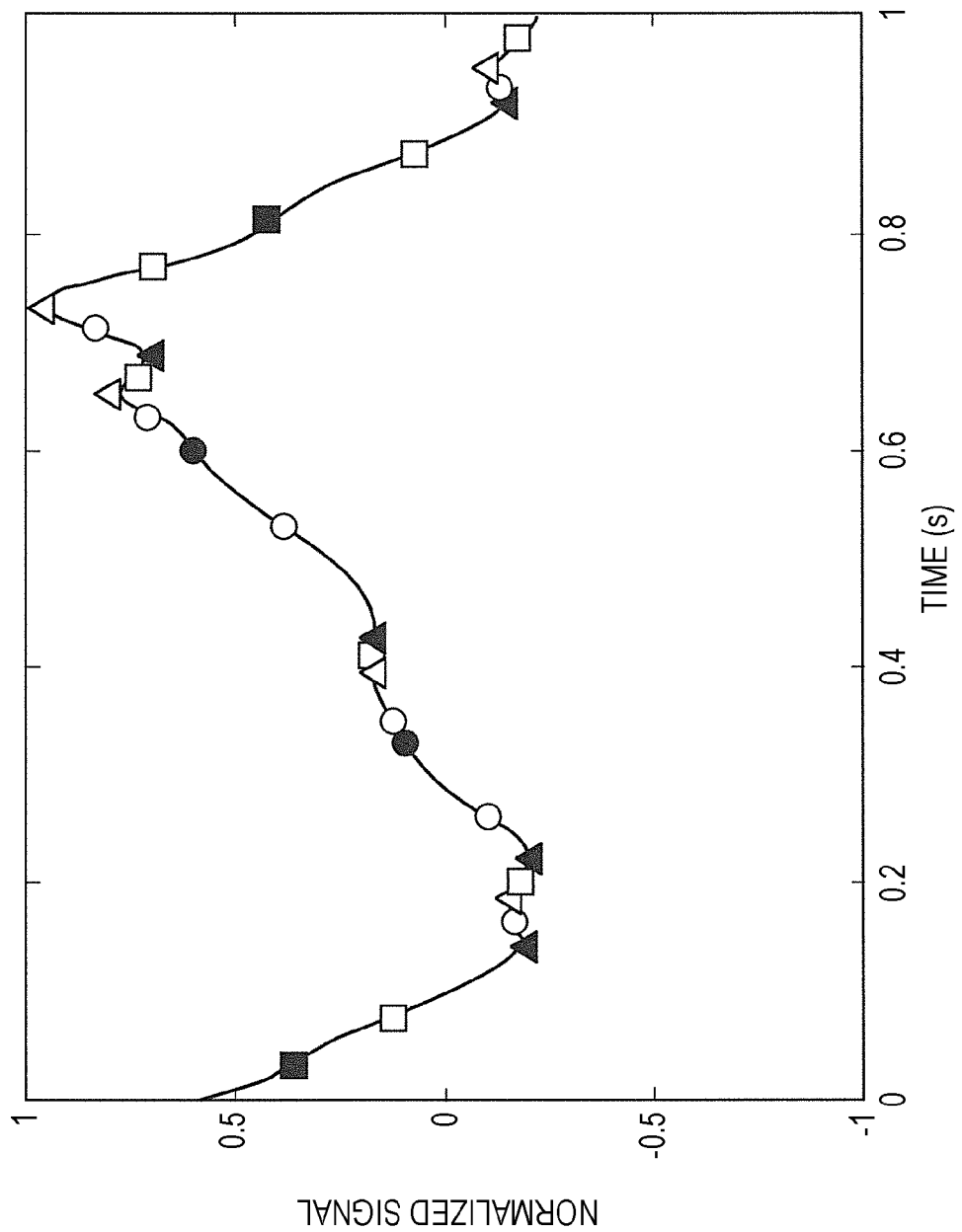
FIG. 6 is a graph illustrating the waveform of a millimeter wave signal for one second according to the first embodiment.

FIG. 6 illustrates a waveform for one second, including about one heartbeat, of the millimeter wave signal illustrated in FIG. 5. In the waveform illustrated in FIG. 6, a plurality of characteristic points are represented by white triangle marks, black triangle marks, white circle marks, black circle marks, white square marks, and black square marks. The meaning of each mark will be described below. Among the plurality of characteristic points, white triangle marks represent local maximum points, black triangle marks represent local minimum points, and white circle marks, black circle marks, white square marks, and black square marks represent inflection points.

Memory Unit 104

The memory unit 104 stores a heartbeat characteristic point pattern. The heartbeat characteristic point pattern includes a plurality of characteristic points and the order of the characteristic points.

FIG. 7 is a table for describing a plurality of characteristic points included in the heartbeat characteristic point pattern. At each of the plurality of characteristic points, a first derivative value (first-order derivative) and a second derivative value (second-order derivative) of the millimeter wave signal have specific values. At some of the plurality of characteristic points, a third derivative value (third-order derivative) of the millimeter wave signal has a specific value. The specific value is not necessarily a concrete value and at least may be information representing any one of a positive sign, a negative sign, and zero.

As illustrated in FIG. 7, each of the plurality of characteristic points is identified by a characteristic point ID. Further, as illustrated in FIG. 7, there are six types of characteristic points.

A characteristic point "peaks (PK)" is a point at which the first derivative value $(ds(t)/dt)$ is 0 and the second derivative value $(d^2s(t)/dt^2)$ is smaller than 0. This point is a local maximum point in a local upward-convex section in the waveform of the millimeter wave signal. This point is represented by a white triangle mark in the graph for the convenience of description given below.

A characteristic point "valleys (VL)" is a point at which the first derivative value $(ds(t)/dt)$ is 0 and the second derivative value $(d^2s(t)/dt^2)$ is larger than 0. This point is a local minimum point in a local downward-convex section in the waveform of the millimeter wave signal. This point is represented by a black triangle mark in the graph.

A characteristic point "rising derivative peak (RDP)" is a point at which the first derivative value $(ds(t)/dt)$ is larger than 0, the second derivative value $(d^2s(t)/dt^2)$ is 0, and the third derivative value $(d^3s(t)/dt^3)$ is smaller than 0. This point is an inflection point at which an increase rate of a signal value of the millimeter wave signal changes when the signal value increases with the lapse of time. This point is represented by a white circle mark in the graph.

A characteristic point "rising derivative valley (RDV)" is a point at which the first derivative value $(ds(t)/dt)$ is larger than 0, the second derivative value $(d^2s(t)/dt^2)$ is 0, and the third derivative value $(d^3s(t)/dt^3)$ is larger than 0. This point is an inflection point at which an increase rate of a signal value of the millimeter wave signal changes when the signal value increases with the lapse of time. This point is represented by a black circle mark in the graph.

A characteristic point "falling derivative peak (FDP)" is a point at which the first derivative value (ds(t)/dt) is smaller than 0, the second derivative value ($d^2$s(t)/$dt^2$) is 0, and the third derivative value ($d^3$s(t)/$dt^3$) is smaller than 0. This point is an inflection point at which a decrease rate of a signal value of the millimeter wave signal changes when the signal value decreases with the lapse of time. This point is represented by a black square mark in the graph.

A characteristic point "falling derivative valley (FDV)" is a point at which the first derivative value (ds(t)/dt) is smaller than 0, the second derivative value ($d^2$s(t)/$dt^2$) is 0, and the third derivative value ($d^3$s(t)/$dt^3$) is larger than 0. This point is an inflection point at which a decrease rate of a signal value of the millimeter wave signal changes when the signal value decreases with the lapse of time. This point is represented by a white square mark in the graph.

The conditions of the first derivative value, second derivative value, and third derivative value that define the above-described six types of characteristic points are stored as characteristic series information in the memory unit 104.

The heartbeat characteristic point pattern does not necessarily include the six types of characteristic points illustrated in FIG. 7. For example, the heartbeat characteristic point pattern may be described by using a point indicating a first local maximum value (characteristic point PK), a first inflection point indicating a negative slope value and a positive third-order derivative value (characteristic point FDV), a point indicating a local minimum value (characteristic point VL), a second inflection point indicating a positive slope value and a negative third-order derivative value (characteristic point RDP), and a point indicating a second local maximum value (characteristic point PK), and may be defined in this order. Here, "this order" means the order in which the characteristic points identified by the identification unit 103 are arranged. The order of the characteristic points may be the following order.

The point indicating the first local maximum value is followed by the first inflection point.
The first inflection point is followed by the point indicating the local minimum value.
The point indicating the local minimum value is followed by the second inflection point.
The second inflection point is followed by the point indicating the second local maximum value.

A point that is not a characteristic point may exist between a certain characteristic point and another characteristic point (for example, between the point indicating the local minimum value and the second inflection point) in the millimeter wave signal.

Figure 8:
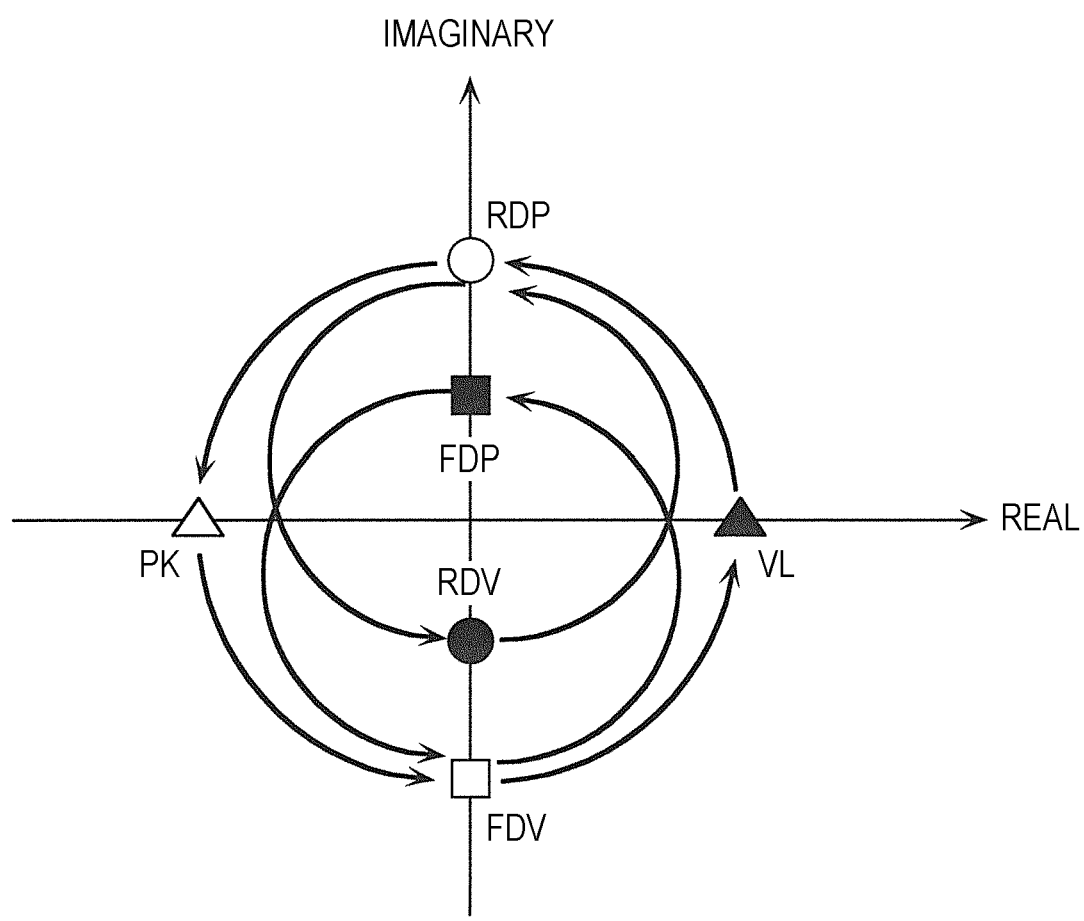
FIG. 8 is a graph illustrating topology information about characteristic points of a heartbeat according to the first embodiment.

FIG. 8 illustrates an example in which the individual characteristic points of heartbeat "VL, RDP, FDP, PK, FDV, and RDV" are assigned on a complex plane. The coordinate values of these characteristic points on the complex plane are (1, 0) for VL, (0, 1) for RDP, (0, 1/2) for FDP, (−1, 0) for PK, (0, −1) for FDV, and (0, −1/2) for RDV. The phase θ of each characteristic point is expressed by an equation $\theta = \tan^{-1}(b/a)$ when the coordinates of each characteristic point are (a, b).

The order of the plurality of characteristic points included in the heartbeat characteristic point pattern is illustrated in FIG. 8. If the heartbeat characteristic point pattern includes two characteristic points PK, one characteristic point FDV, one characteristic point VL, and one characteristic point RDP, one of the characteristic points PK is first described and is followed by the characteristic points FDV, VL, and RDP, and the other of the characteristic points PK in this order in accordance with the outermost arrows and the order of the characteristic points illustrated in FIG. 8.

Acquisition Unit 105

The acquisition unit 105 refers to a heartbeat characteristic point pattern and acquires, from among the plurality of characteristic points identified by the identification unit 103, a first characteristic point set including a plurality of characteristic points that are arranged in an order identical to that of the characteristic points of the heartbeat characteristic point pattern.

Figure 9:
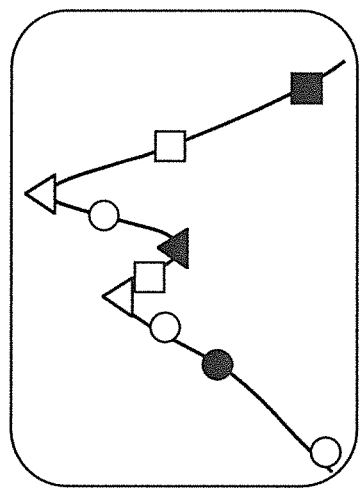
FIG. 9 is a diagram illustrating an example of a heartbeat characteristic point pattern and a plurality of characteristic points included in a millimeter wave signal according to the first embodiment.

FIG. 9 illustrates an example of the heartbeat characteristic point pattern and a plurality of characteristic points included in a millimeter wave signal. FIG. 9(a) illustrates an example of the heartbeat characteristic point pattern "RDP, RDV, RDP, PK, FDV, VL, RDP, PK, FDV, FDP". The acquisition unit 105 refers to the heartbeat characteristic point pattern and performs pattern matching or the like on the plurality of characteristic points included in the millimeter wave signal and identified by the identification unit 103. Accordingly, the acquisition unit 105 acquires a plurality of characteristic points included in one heartbeat as illustrated in FIG. 9(b). In other words, the acquisition unit 105 acquires the above-described first characteristic point set as one heartbeat.

Figure 10:
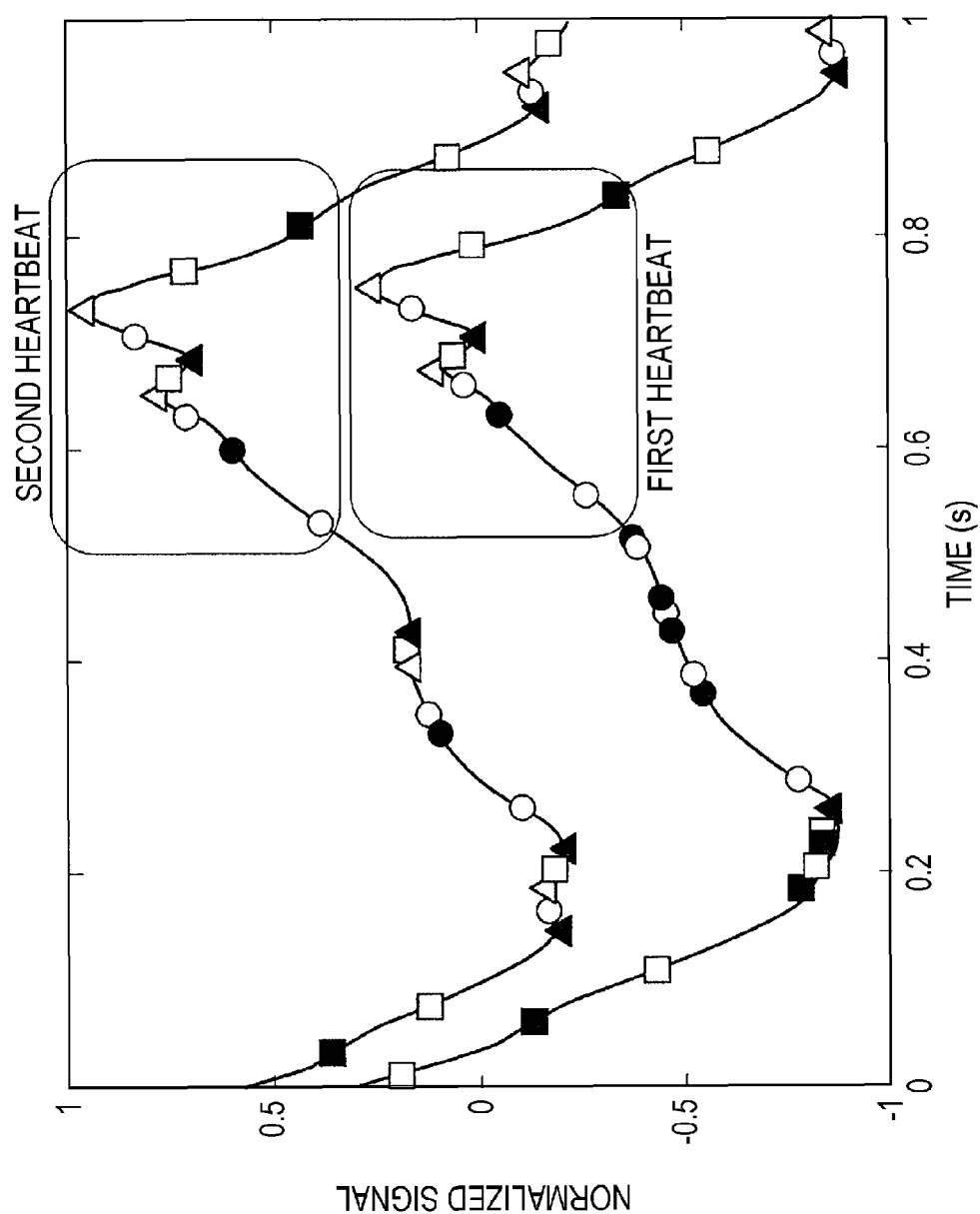
FIG. 10 is a graph illustrating an example of acquisition of a plurality of characteristic points according to the first embodiment.

FIG. 10 illustrates an example of acquisition of a plurality of characteristic points. FIG. 10 illustrates a waveform of a millimeter wave signal for one second including a first heartbeat and a waveform of a millimeter wave signal for one second including a second heartbeat subsequent to the first heartbeat, one above the other.

As can be seen in FIG. 10, each of the waveforms (one heartbeat) has a shape representing two local maximum points close to each other. Such a shape is called a double peak shape. Also, it can be seen that the plurality of characteristic points in each waveform has a series "RDP, RDV, RDP, PK, FDV, VL, RDP, PK, FDV, FDP". In contrast, in a region other than the region including the double peak, for example, in a foot portion which is a region including a point indicating a minimum value, the series of a plurality of characteristic points varies between the first heartbeat and the second heartbeat. With pattern matching (also referred to as matching calculation) being performed with reference to a heartbeat characteristic point pattern, each heartbeat can be accurately detected while suppressing detection errors of heartbeats.

The acquisition unit 105 may define the order of a plurality of characteristic points of a heartbeat by referring to the topology information illustrated in FIG. 8. The plurality of characteristic points in the defined order may be used as a heartbeat characteristic point pattern.

The acquisition unit 105 converts, with use of the coordinate values on the complex plane indicated by the topology information, heartbeat data into a heartbeat characteristic point series described by using phase information.

Figure 11:
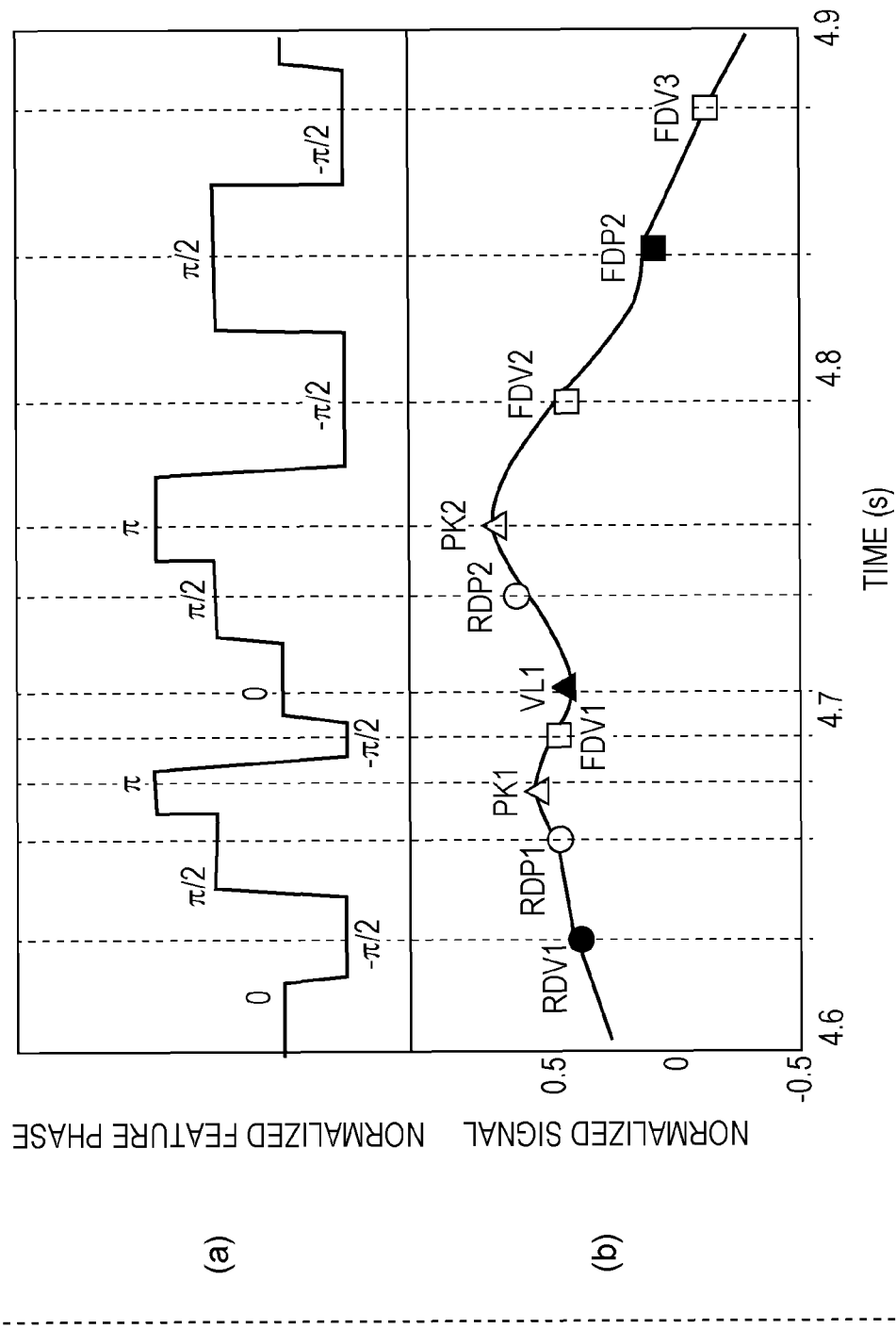
FIG. 11 is a graph for describing a heartbeat characteristic point series indicating phases according to the first embodiment.

FIG. 11 is a graph for describing a heartbeat characteristic point series described by using phase information. FIG. 11(b) illustrates heartbeat data and FIG. 11(a) illustrates a heartbeat characteristic point series and the values thereof acquired through conversion. The amplitude values of the individual characteristic points in the heartbeat data are converted into phase values. For example, the amplitude value of a characteristic point RDV1 is converted into a phase value −π/2, the amplitude value of a characteristic point RDP1 is converted into a phase value π/2, the amplitude value of a characteristic point PK1 is converted into a phase value π, the amplitude value of a characteristic point FDV1 is converted into a phase value $-\pi/2$, the amplitude value of a characteristic point VL1 is converted into a phase value 0, the amplitude value of a characteristic point RDP2 is converted into a phase value $\pi/2$, and the amplitude value of a characteristic point PK2 is converted into a phase value $\pi$. The acquisition unit 105 correlates, based on the phase values, the characteristic points included in the heartbeat characteristic point pattern with the characteristic points in the heartbeat data, and acquires a plurality of characteristic points corresponding to the characteristic points included in the heartbeat characteristic point pattern. In the case of acquiring the characteristic points corresponding to the characteristic points included in the heartbeat characteristic point pattern from the heartbeat data, a better result can be acquired by using the phase values of the characteristic points included in the heartbeat data than in the case of using actual values of the characteristic points included in the heartbeat data, that is, amplitude values. For example, at a portion having a double peak shape including two local maximum points close to each other, indicating a characteristic of a heartbeat in the heartbeat data, such as a portion where the characteristic points RDP1, PK1, FDV1, VL1, RDP2, PK2, and FDV2 are acquired, the value (amplitude value) of the heartbeat data shows slight changes, but the phase in the topology information shows a remarkable characteristic, that is, the phase value $\pi/2$ changes to $\pi$, $-\pi/2$, 0, $\pi/2$, $\pi$, and $-\pi/2$. Accordingly, more accurate heartbeats, heartbeats corresponding to a heartbeat characteristic point pattern based on correlation, and heartbeat intervals can be extracted. Furthermore, with use of phase values instead of values of heartbeat data, calculation can be easily performed the amount of calculation can be reduced.

The acquisition unit 105 may further acquire a second characteristic point set different from the first characteristic point set in time of the millimeter wave signal. That is, the acquisition unit 105 refers to a heartbeat characteristic point pattern and acquires, from among the plurality of characteristic points identified by the identification unit 103, a second characteristic point set that is different from the first characteristic point set and that includes a plurality of characteristic points arranged in an order identical to that of the characteristic points of the heartbeat characteristic point pattern. The acquisition unit 105 is able to acquire different heartbeats, that is, the first characteristic point set and the second characteristic point set. In other words, the acquisition unit 105 acquires each of heartbeats.

Output Unit 106

The output unit 106 outputs, as heartbeat information on a user, information including a time based on the characteristic points included in the above-described first characteristic point set that has been acquired. Specifically, the output unit 106 outputs, as heartbeat information, information including a heartbeat timing which is a time when a heartbeat occurs, based on an acquired heartbeat (first characteristic point set). For example, the output unit 106 outputs a heartbeat timing with reference to information about timing (hereinafter referred to as timing information) that is stored in the memory unit 104 together with a heartbeat characteristic point pattern. For example, as illustrated in FIG. 9, the memory unit 104 stores a pair of pieces of information: the heartbeat characteristic point pattern "RDP, RDV, RDP, PK, FDV, VL, RDP, PK, FDV, FDP" and timing information representing a heartbeat timing which is a time when the characteristic point "VL" indicating a local minimum value appears. Based on the timing information stored in the memory unit 104, the output unit 106 outputs, as a heartbeat timing, the time of the characteristic point VL included in the acquired first characteristic point set. If the second characteristic point set is also acquired by the acquisition unit 105, the output unit 106 may output heartbeat information including a time based on the characteristic points included in the second characteristic point set. Accordingly, the output unit 106 is able to output the heartbeat timing of each heartbeat.

Figure 12:
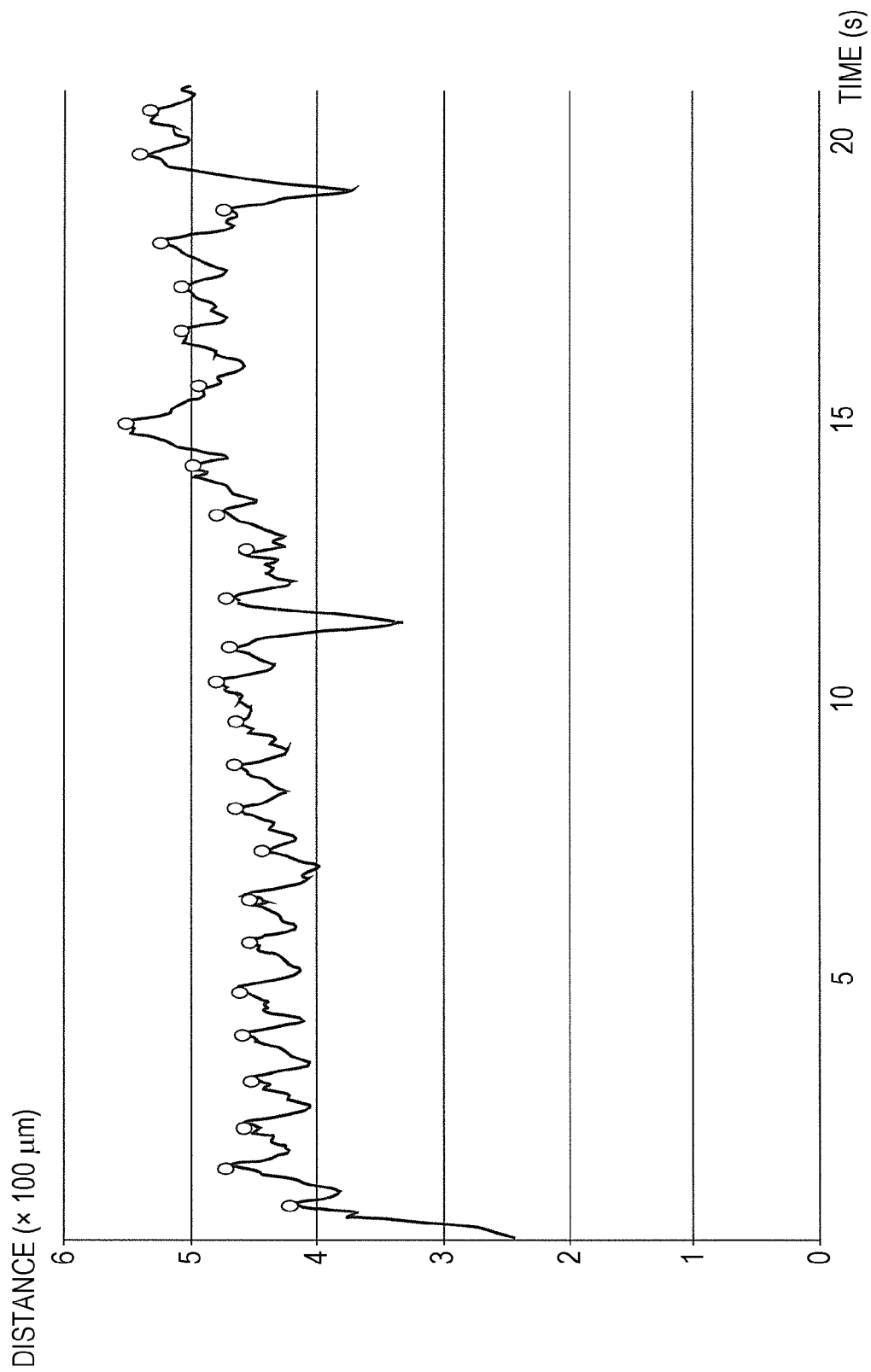
FIG. 12 is a graph for describing heartbeat timings according to the first embodiment.
Figure 13:
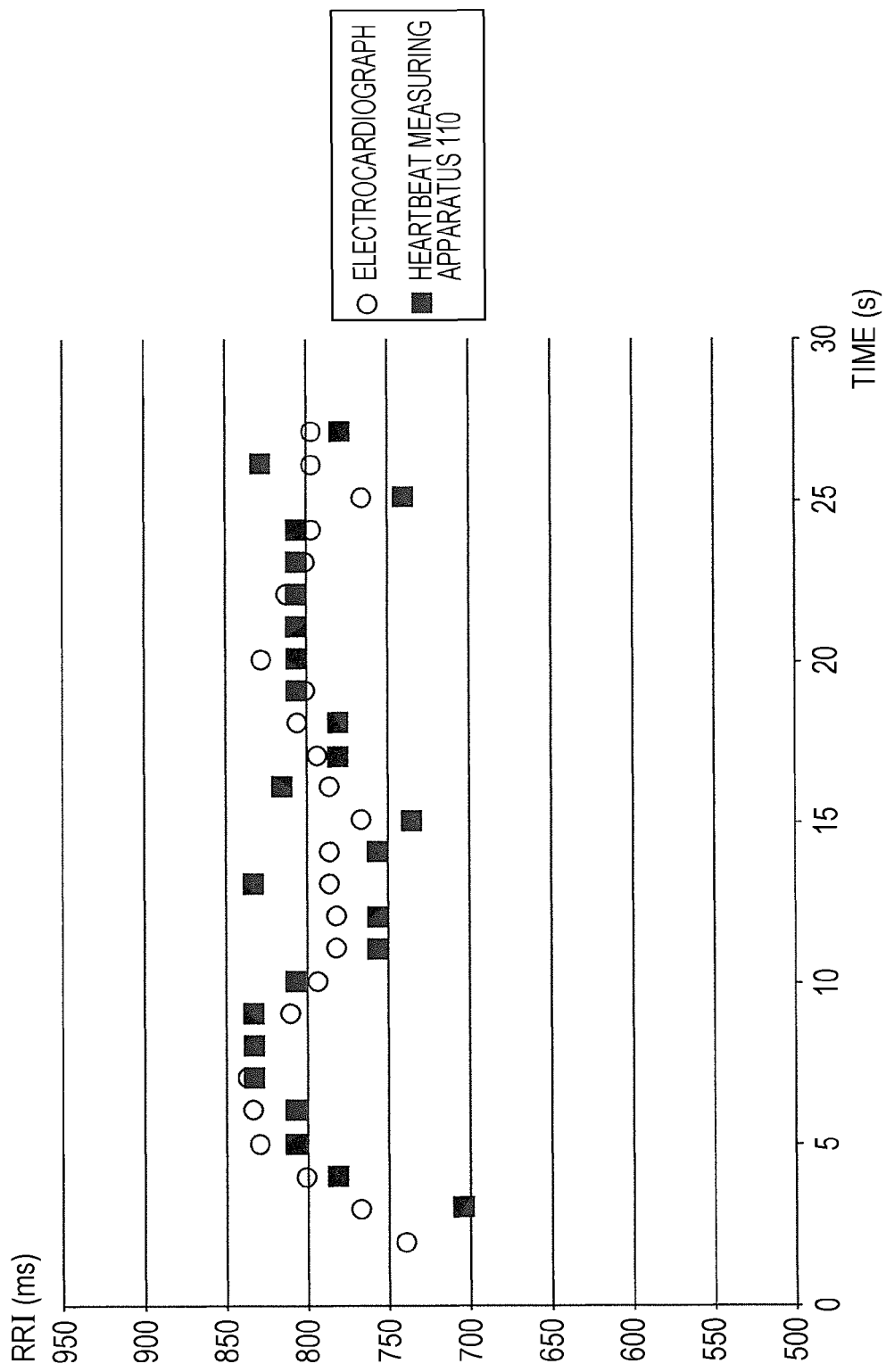
FIG. 13 is a graph illustrating intervals of output heartbeat timings and intervals of R waves acquired by an electrocardiograph according to the first embodiment.

FIG. 12 is a graph for describing heartbeat timings. The output unit 106 outputs, as heartbeat timings, times when characteristic points (white circles illustrated in FIG. 12) indicated by the timing information appear. FIG. 13 is a graph illustrating the intervals of R waves (heartbeats) acquired by an electrocardiograph and the intervals of output heartbeat timings. As illustrated in FIG. 12, the time interval of heartbeats (so-called R-R interval (RRI)) is not constant and fluctuates in the range from about 600 ms to 950 ms. Also, as illustrated in FIG. 13, the intervals of heartbeat timings output by the heartbeat measuring apparatus 110 has a very high correlation with RRI measured by the electrocardiograph. That is, the heartbeat measuring apparatus 110 according to the first embodiment outputs correct heartbeat timings.

If the acquisition unit 105 acquires the characteristic points included in the first characteristic point set and the characteristic points included in the second characteristic point set, the output unit 106 may output a heartbeat interval which is a difference between the heartbeat timings thereof. Specifically, the output unit 106 outputs heartbeat information on a user including a time difference which is a difference between the time of a characteristic point PK included in the first characteristic point set and the time of a characteristic point PK included in the second characteristic point set; a difference between the time of a characteristic point VL included in the first characteristic point set and the time of a characteristic point VL included in the second characteristic point set; a difference between the time of a characteristic point RDP included in the first characteristic point set and the time of a characteristic point RDP included in the second characteristic point set; a difference between the time of a characteristic point RDV included in the first characteristic point set and the time of a characteristic point RDV included in the second characteristic point set; a difference between the time of a characteristic point FDP included in the first characteristic point set and the time of a characteristic point FDP included in the second characteristic point set; or a difference between the time of a characteristic point FDV included in the first characteristic point set and the time of a characteristic point FDV included in the second characteristic point set. In this way, the output unit 106 outputs heartbeat information on a user further including a time difference which is a difference between a time related to the characteristic points included in the first characteristic point set and a time related to the characteristic points included in the second characteristic point set.

Presentation Unit 107

The presentation unit 107 presents heartbeat information on a user (information regarding heartbeat timings) that has been output.

Figure 14:
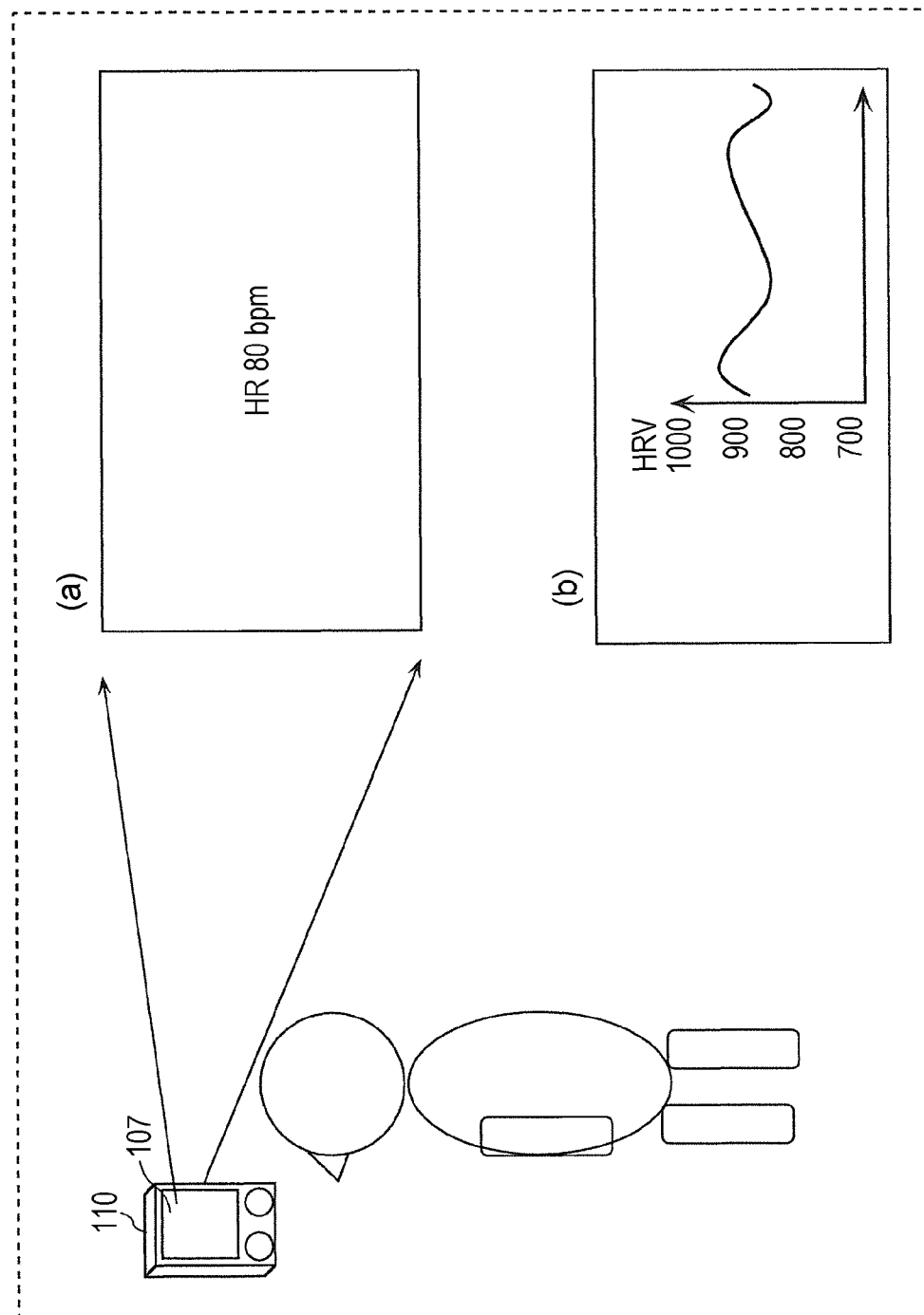
FIG. 14 is an explanatory diagram of a presentation unit according to the first embodiment.

FIG. 14 is a diagram for describing an example of the presentation unit 107. The presentation unit 107 presents an average heart rate per minute (bpm), as illustrated in FIG. 14(*a*). Alternatively, the presentation unit 107 presents heartbeat intervals (heart rate variability (HRV)), as illustrated in FIG. 14(*b*). The heartbeat measuring apparatus 110 according to the first embodiment does not necessarily include the presentation unit 107. In this case, the heartbeat information output from the output unit 106 is presented by another apparatus.

Operation of Heartbeat Measuring Apparatus 110

Figure 15:
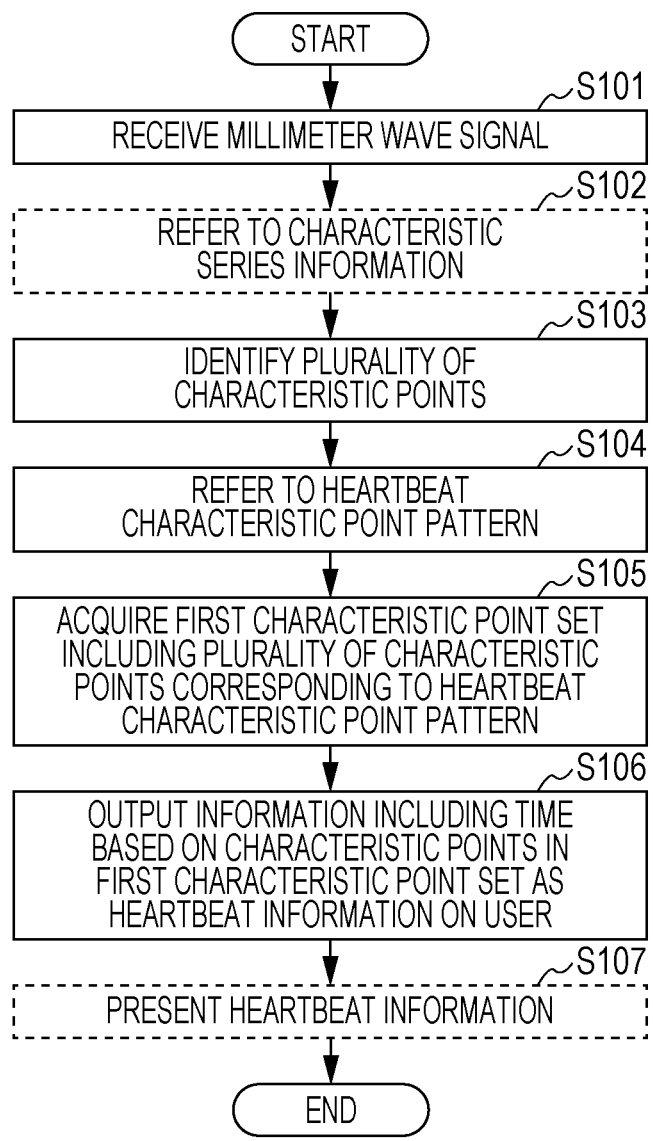
FIG. 15 is a flowchart of a process performed by the heartbeat measuring apparatus according to the first embodiment.

FIG. 15 is a flowchart of a process performed by the heartbeat measuring apparatus 110 according to the first embodiment.

In step S101, the reception unit 101 receives a millimeter wave signal (heartbeat data) reflected by a user.

In step S102, the identification unit 103 refers to characteristic series information stored in the memory unit 104. If the characteristic series information is set in the identification unit 103 in advance, such reference to the characteristic series information is not necessarily performed. In step S103, the identification unit 103 identifies, based on the characteristic series information, a plurality of characteristic points of the acquired millimeter wave signal in time series.

In step S104, the acquisition unit 105 refers to a heartbeat characteristic point pattern stored in the memory unit 104. In step S105, the acquisition unit 105 acquires, as a heartbeat, a first characteristic point set including a plurality of characteristic points corresponding to the heartbeat characteristic point pattern. That is, the acquisition unit 105 acquires, from among the plurality of characteristic points identified in step S103, the first characteristic point set including the plurality of characteristic points arranged in an order identical to that of the characteristic points of the heartbeat characteristic point pattern.

In step S106, the output unit 106 outputs, as heartbeat information on the user, information including a time (heartbeat timing) based on the characteristic points included in the acquired first characteristic point set. In step S107, the presentation unit 107 presents the heartbeat information on the user including the heartbeat timing output from the output unit 106. The presentation of the information is not necessarily performed.

In the first embodiment, a description has been given by using the pattern illustrated in FIG. 9 as an example of a heartbeat characteristic point pattern, but the heartbeat characteristic point pattern is not limited thereto. The acquisition unit 105 may acquire the above-described characteristic point set by performing pattern matching with reference to another heartbeat characteristic point pattern stored in the memory unit 104.

Figure 16:
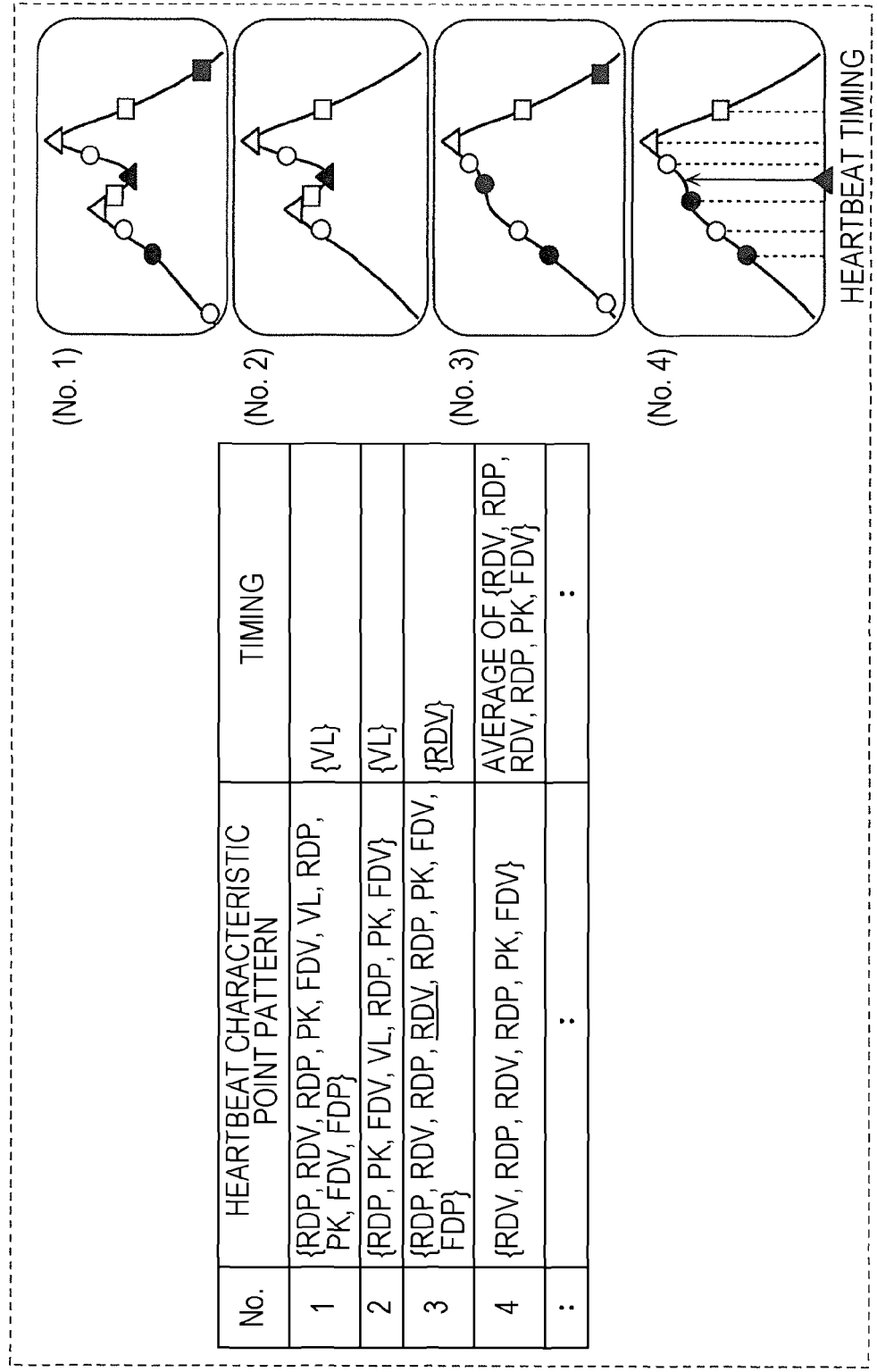
FIG. 16 is an explanatory diagram of a plurality of heartbeat characteristic point patterns according to the first embodiment.

FIG. 16 is a diagram for describing a plurality of heartbeat characteristic point patterns. As illustrated in FIG. 16, the memory unit 104 stores a heartbeat characteristic point pattern No. 1 "RDP, RDV, RDP, PK, FDV, VL, RDP, PK, FDV, FDP" and other heartbeat characteristic point patterns Nos. 2 to 4.

The heartbeat data has a distinctive shape, which is a double peak shape having two local maximum points close to each other. This shape can be described by using the characteristic points RDP, PK, FDV, VL, RDP, PK, and FDV. The portion of the millimeter wave signal defined without using these characteristic points may be changed by an influence of noise or the like. Thus, the acquisition unit 105 may refer to the heartbeat characteristic point pattern No. 2 "RDP, PK, FDV, VL, RDP, PK, FDV" that includes characteristic pints related to the double peak shape and that does not include the other characteristic points and may perform pattern matching thereon. Accordingly, noise-robust heartbeat data can be acquired.

The memory unit 104 may store a heartbeat characteristic point pattern in which the first local maximum point of the double peak is blunt, for example, the heartbeat characteristic point pattern No. 3 "RDP, RDV, RDP, RDV, RDP, PK, FDV, FDP". The shape of the heartbeat data of each subject or the same subject varies among individual heartbeats, and a double peak may or may not be detected. With the heartbeat characteristic point pattern in which the first peak of the double peak is blunt (the heartbeat characteristic point pattern No. 3) being stored in the memory unit 104, heartbeats can be accurately acquired.

The acquisition unit 105 may perform weighted calculation when performing pattern matching. For example, if a total sum of a plurality of characteristic points corresponding to a heartbeat characteristic point pattern is equal to or larger than a threshold, the acquisition unit 105 may acquire a characteristic point set including the plurality of characteristic points as a heartbeat. Alternatively, the acquisition unit 105 may assign a large weight to a distinctive series (for example, a double peak shape portion) and calculate a total sum of weighted degrees of match for the plurality of characteristic points. If the total sum is equal to or larger than the threshold, the acquisition unit 105 may acquire a characteristic point set including the plurality of characteristic points as a heartbeat. Each of the above-described weights is a coefficient represented by w=0 to 1, and the total sum is calculated by $\Sigma w_i \times K$. If the characteristic points included in the heartbeat characteristic point pattern match the characteristic points included in heartbeat data, K equals 1. If the characteristic points do not match, K equals 0.

In the first embodiment, a heartbeat timing has been described as a time when a local minimum point (characteristic point VL) between two local maximum points close to each other having a double-peak shape appears, but the heartbeat timing is not limited thereto. A point corresponding to a valley (characteristic point VL) may be estimated from a series of a plurality of characteristic points and the time when the point appears may be used as a heartbeat timing. This will be described in detail below.

The heartbeat characteristic point pattern No. 3 is a pattern in which the first peak of the double peak is blunt. There is no local minimum point (characteristic point VL) in this pattern. However, there is a characteristic point corresponding to the characteristic point VL in the heartbeat characteristic point pattern No. 3. This characteristic point is an inflection point and is the fourth characteristic point RDV included in the heartbeat characteristic point pattern No. 3 (the second black circle mark from the left in FIG. 16 or RDV with an under bar). Thus, the memory unit 104 stores timing information indicating that the time when the characteristic point RDV appears is to be output as a heartbeat timing. Accordingly, a robust heartbeat timing can be output.

Alternatively, the acquisition unit 105 may calculate the heartbeat timing corresponding to the characteristic point VL by using characteristic points other than the characteristic point VL. Specifically, the acquisition unit 105 refers to the heartbeat characteristic point pattern No. 4 "RDV, RDP, PDV, RDP, PK, FDV" stored in the memory unit 104 and acquires a heartbeat that matches this pattern. The memory unit 104 stores, for example, timing information representing an average time of "RDV, RDP, PDV, RDP, PK, FDV". Thus, the output unit 106 outputs, as a heartbeat timing, an average time of the times when the characteristic points "RDV, RDP, PDV, RDP, PK, FDV" appear. Accordingly, more robust heartbeat timing can be output even if the characteristic point VL is not acquired.

The output unit 106 may output, as a heartbeat timing, a time when the characteristic point PK at the first peak of the double peak appears, a time when the characteristic point PK at the second peak of the double peak appears, or a time when another characteristic point appears. Furthermore, the output unit 106 may output, as a heartbeat timing, a time that is required in each application, such as an average of times when a plurality of characteristic points appear. For example, if the end timing of ventricular dilation is required, the output unit 106 outputs a time when the characteristic point PK at the first peak of the double peak appears as the heartbeat timing. If the end timing of atrial contraction is required, the output unit 106 outputs a time when the characteristic point VL at the valley of the double peak appears as the heartbeat timing. If the end timing of atrial dilation is required, the output unit 106 outputs a time when the characteristic point PK at the second peak of the double peak appears as the heartbeat timing. Accordingly, an appropriate heartbeat timing can be output for each specific timing of the heartbeat that is required.

According to the first embodiment, heartbeat characteristic point patterns are stored in advance, but the heartbeat characteristic point patterns are not necessarily stored in advance. For example, the heartbeat measuring apparatus 110 may automatically extract a pattern that often appears from a series of a plurality of characteristic points (IDs) included in heartbeat data. The extraction may be performed by using, for example, the FP-growth method. The heartbeat measuring apparatus 110 may use the pattern extracted by using this method as a heartbeat characteristic point pattern. This will be described with reference to FIG. 10. As illustrated in FIG. 10, a series of a plurality of characteristic points is specified in each of the first and second heartbeats. In the time period from about 0.6 to 0.8 seconds, a plurality of characteristic points "RDP, RDV, RDP, PK, FDV, VL, RDP, PK, FDV, FDP" are arranged in this order both in the first and second heartbeats. In contrast, in the time period from about 0.1 to 0.5 seconds, the pattern of the series is different between the first and second heartbeats. Thus, the heartbeat measuring apparatus 110 extracts, from the series of the plurality of characteristic points, "RDP, RDV, RDP, PK, FDV, VL, RDP, PK, FDV, FDP" as a pattern that often appears by using the above-mentioned FP-growth method, which is a frequent pattern extraction method. The heartbeat measuring apparatus 110 acquires a heartbeat by using the extracted pattern as a heartbeat characteristic point pattern. Accordingly, a heartbeat characteristic point pattern corresponding to each piece of heartbeat data can be extracted and a heartbeat can be acquired.

As described above, the heartbeat measuring apparatus 110 according to the first embodiment includes the reception unit 101, the identification unit 103, the memory unit 104, the acquisition unit 105, and the output unit 106. The reception unit 101 receives a millimeter wave signal reflected by a user. The identification unit 103 identifies a plurality of characteristic points of the received millimeter wave signal in time series, the plurality of characteristic points including a local maximum point, a local minimum point, and an inflection point associated with information representing a positive or negative sign of a slope and information representing a positive or negative sign of a third-order derivative. The memory unit 104 stores a heartbeat characteristic point pattern. The heartbeat characteristic point pattern is formed of characteristic points including a point indicating a first local maximum value, a first inflection point having a negative slope and a positive third-order derivative, a point indicating a local minimum value, a second inflection point having a positive slope and a negative third-order derivative, and a point indicating a second local maximum value, and is defined in this order. The acquisition unit 105 refers to the heartbeat characteristic point pattern and acquires, from the plurality of characteristic points that have been identified, a first characteristic point set including a plurality of characteristic points arranged in an order identical to that of the characteristic points of the heartbeat characteristic point pattern. The output unit 106 outputs information including a time based on the characteristic points included in the first characteristic point set as heartbeat information on the user.

The point indicating the first local maximum value and the point indicating the second local maximum value correspond to the above-described characteristic point PK, and the point indicating the local minimum value at the valley corresponds to the above-described characteristic point VL. The inflection point associated with information representing a positive or negative sign of a slope and information representing a positive or negative sign of a third-order derivative corresponds to one of the above-described characteristic points RDP, RDV, FDP, and FDV. The first inflection point having a negative slope and a positive third-order derivative correspond to the characteristic point FDV. The second inflection point having a positive slope and a negative third-order derivative corresponds to the characteristic point RDP.

In the first embodiment, a first characteristic point set corresponding to a heartbeat characteristic point pattern is acquired as a heartbeat, and a time based on the characteristic points included in the first characteristic point set is measured as a heartbeat timing. Accordingly, the technique disclosed in the first embodiment suppresses blunting of a local maximum point caused by frequency analysis according to the related art and shift of the position of the local maximum point due to phase shift caused by filtering according to the related art. As a result, a correct heartbeat timing can be measured.

In the first embodiment, the acquisition unit 105 may further acquire, from among the plurality of characteristic points that have been identified, a second characteristic point set whose time in the millimeter wave signal is different from that of the first characteristic point set, the second characteristic point set including a plurality of characteristic points arranged in an order identical to that of the characteristic points of the heartbeat characteristic point pattern, with reference to the heartbeat characteristic point pattern. In this case, the output unit 106 outputs heartbeat information on the user further including a time difference which is a difference between a time based on the characteristic points included in the first characteristic point set and a time based on the characteristic points included in the second characteristic point set.

For example, the output unit 106 may output heartbeat information on the user including the above-described time difference, which is the difference between the time of the point indicating the first local maximum value included in the first characteristic point set and the time of the point indicating the first local maximum value included in the second characteristic point set, the difference between the time of the first inflection point included in the first characteristic point set and the time of the first inflection point included in the second characteristic point set, the difference between the time of the point indicating the local minimum value included in the first characteristic point set and the time of the point indicating the local minimum value included in the second characteristic point set, the difference between the time of the second inflection point included in the first characteristic point set and the time of the second inflection point included in the second characteristic point set, or the difference between the time of the point indicating the second local maximum value included in the first characteristic point set and the time of the point indicating the second local maximum value included in the second characteristic point set.

Accordingly, a correct time difference in heartbeat timing is output, and a heartbeat interval can be correctly measured.

Second Embodiment

In the first embodiment, a description has been given of the apparatus that acquires each heartbeat with high accuracy and outputs heartbeat timings. In the measurement of heartbeats that is daily performed, fluctuation of heartbeat intervals may be used in addition to acquisition of each heartbeat. Fluctuation of heartbeat intervals is considered as an index indicating user's stress, health, or mental state. In a second embodiment, a description will be given of a heartbeat measuring apparatus that measures heartbeat intervals with higher accuracy.

A heartbeat measuring apparatus 111 according to the second embodiment will be described.

Figure 17:
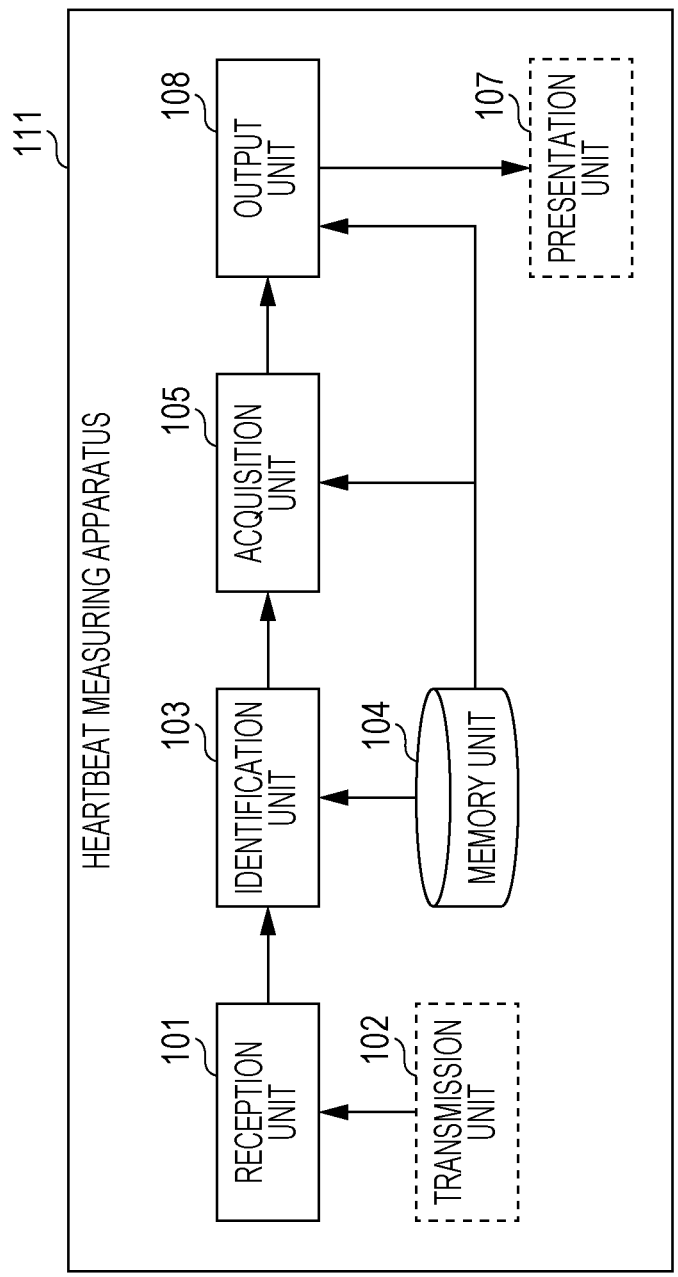
FIG. 17 is a block diagram illustrating the configuration of a heartbeat measuring apparatus according to a second embodiment.

FIG. 17 is a block diagram illustrating the configuration of the heartbeat measuring apparatus 111 according to the second embodiment.

The heartbeat measuring apparatus 111 according to the second embodiment includes the reception unit 101, the transmission unit 102, the identification unit 103, the memory unit 104, the acquisition unit 105, an output unit 108, and the presentation unit 107. Among the elements illustrated in FIG. 17, the same elements as those illustrated in FIG. 2 are denoted by the same reference numerals and the description thereof is omitted. The heartbeat measuring apparatus 111 according to the second embodiment includes the output unit 108 instead of the output unit 106 of the heartbeat measuring apparatus 110 according to the first embodiment.

The acquisition unit 105 according to the second embodiment refers to a heartbeat characteristic point pattern and acquires, from among a plurality of characteristic points that have been identified, the above-described first characteristic point set including a plurality of characteristic points arranged in an order identical to that of the characteristic points of the heartbeat characteristic point pattern, as in the first embodiment. That is, the acquisition unit 105 acquires a first heartbeat corresponding to the first characteristic point set.

The output unit 108 according to the second embodiment determines, among the plurality of characteristic points that have been identified, a corresponding characteristic point that corresponds to a reference point which is a characteristic point in the heartbeat for the first characteristic point set (first heartbeat) and that is included in a heartbeat different from the first heartbeat (second heartbeat). The output unit 108 outputs heartbeat information on the user further including a time difference which is a difference between a time of the reference point and a time of the corresponding characteristic point. The time difference corresponds to a heartbeat interval. Specifically, the output unit 108 determines the corresponding characteristic point, which is a characteristic point of the second heartbeat corresponding to the characteristic point of the first heartbeat, among the plurality of characteristic points included in each heartbeat identified by the identification unit 103. The output unit 108 calculates a heartbeat interval by using a time interval between these characteristic points. The output unit 108 outputs the heartbeat interval calculated in this manner to the presentation unit 107.

Fluctuation of heartbeat intervals is considered as an index indicating user's stress, health, or mental state, and calculation of correct heartbeat intervals is required. In the related art, frequency analysis or filtering is performed on acquired heartbeat data and a peak is extracted, thereby calculating the heartbeat timing of one heartbeat. Such calculation is performed on each peak. The interval between two heartbeat timings that have been calculated is regarded as a heartbeat interval, and the fluctuation thereof is calculated. However, in the frequency analysis or filtering according to the related art, a peak is blunted or the position of the peak is shifted due to phase shift in the filtering, and it is difficult to correctly calculate fluctuation of heartbeat intervals. Further, since only the heartbeat interval calculated for each peak is used, it is difficult to correctly calculate fluctuation of heartbeat intervals.

In the first embodiment, the heartbeat timing of each heartbeat can be measured, and heartbeat intervals can be measured based on the intervals between the heartbeat timings. That is, in the first embodiment, a heartbeat interval can be measured for each heartbeat. In contrast, in the second embodiment, a heartbeat interval is measured for each characteristic point. Specifically, in the second embodiment, a characteristic point of a second heartbeat corresponding to a characteristic point of a first heartbeat is determined as a corresponding characteristic point, and the time interval between the characteristic point and the corresponding characteristic point is measured as a heartbeat interval. Accordingly, more correct heartbeat intervals can be measured.

Figure 18:
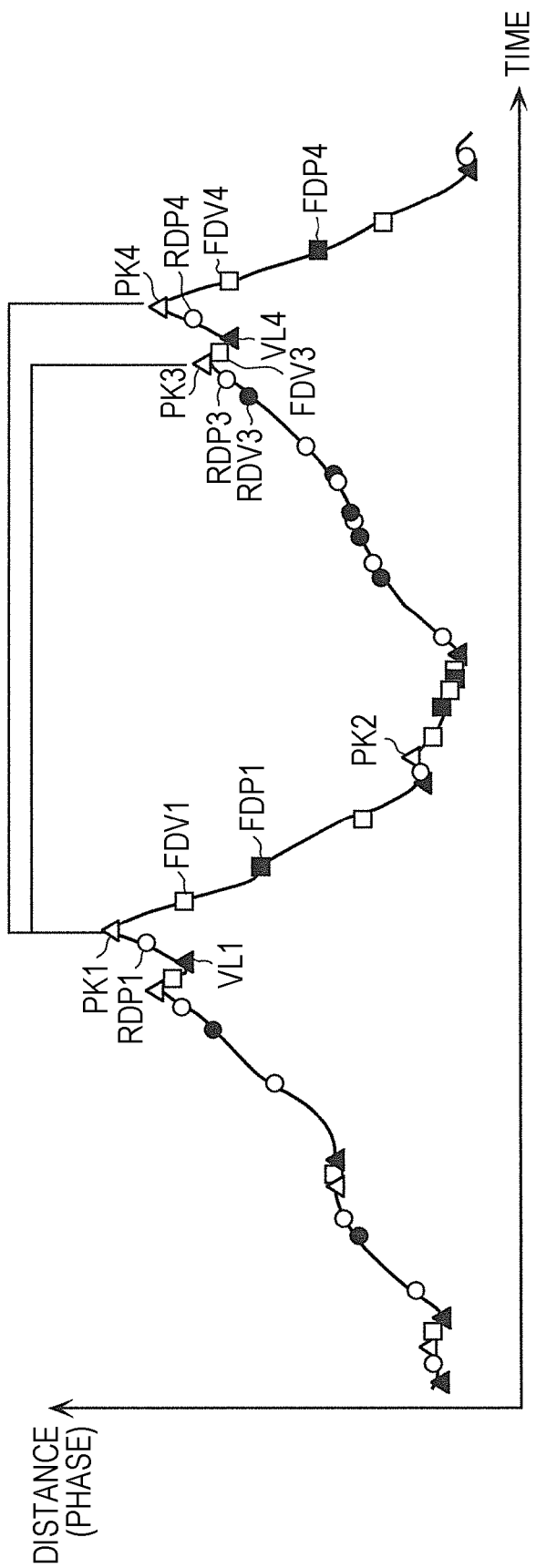
FIG. 18 is a graph for describing calculation of a heartbeat interval according to the second embodiment.

FIG. 18 is a graph for describing calculation of a heartbeat interval. FIG. 18 illustrates heartbeat data acquired by the reception unit 101 and a series of characteristic points identified by the identification unit 103. The output unit 108 determines, for each characteristic point of the first heartbeat, a characteristic point of the second heartbeat corresponding thereto, as a corresponding characteristic point.

A heartbeat interval of a human being is about 80 bpm (interval=750 ms) in the daily life and usually fluctuates in the range from 40 bpm to 180 bpm. Thus, the output unit 108 calculates characteristic points by using a certain threshold. The certain threshold is, for example, 500 ms, which is the minimum value of a heartbeat interval, or 1200 ms, which is the maximum value of a heartbeat interval.

Specifically, as illustrated in FIG. 18, the output unit 108 searches for a characteristic point having an ID that matches a characteristic point PK1, which is a reference point of the first heartbeat. As a result, the output unit 108 finds, in FIG. 18, characteristic points PK2, PK3, and PK4 as characteristic points having an ID that matches the characteristic point PK1. Here, the interval between the characteristic point PK1 as a reference point and the characteristic point PK2 is smaller than the threshold (500 ms). Thus, the output unit 108 excludes the characteristic point PK2 from the candidates for the characteristic point corresponding to the characteristic point PK1 (corresponding characteristic point) and regards the characteristic points PK3 and PK4 as the candidates. Subsequently, the output unit 108 determines the corresponding characteristic point, based on the degree of match between a series including a candidate and the characteristic points before and after the candidate and a series including the reference characteristic point PK1 and the characteristic points before and after the reference characteristic point PK1. For example, the output unit 108 calculates the degree of match by using the characteristic point PK1 and the two characteristic points before and after the characteristic point PK1, and the candidate characteristic point and the two characteristic points before and after the candidate characteristic point. The degree of match is the degree of match between IDs of characteristic points. The series including the characteristic point PK1 and the characteristic points before and after the characteristic point PK1 is "VL1, RDP1, PK1, FDV1, FDP1". The series including the candidate characteristic point PK3 and the characteristic points before and after the candidate characteristic point PK3 is "RDV3, RDP3, PK3, FDV3, VL4". In these series, the IDs of the first characteristic points VL1 and RDV3 are different from each other, and the IDs of the last characteristic points FDP1 and VL4 are different from each other. On the other hand, in these series, the IDs of the second characteristic points RDP1 and RDP3 match each other, the IDs of the third characteristic points PK1 and PK3 match each other, and the IDs of the fourth characteristic points FDV1 and FDV3 match each other. Thus, in this case, the output unit 108 obtains a calculation result 0.6 by dividing 3 by 5 as the degree of match between these series. On the other hand, the series including the candidate characteristic point PK4 and the characteristic points before and after the candidate characteristic point PK4 is "VL4, RDP4, PK4, FDV4, FDP4". Thus, in this case, the output unit 108 obtains a calculation result 1 by dividing 5 by 5 as the degree of match between the series including the characteristic point PK1 and the characteristic points before and after the characteristic point PK1, and the series including the characteristic point PK4 and the characteristic points before and after the characteristic point PK4. Accordingly, the output unit 108 determines, among the candidate characteristic points PK3 and PK4, the characteristic point PK4 as the characteristic point corresponding to the characteristic point PK1 (corresponding characteristic point). The output unit 108 performs such calculation for each characteristic point.

Figure 19:
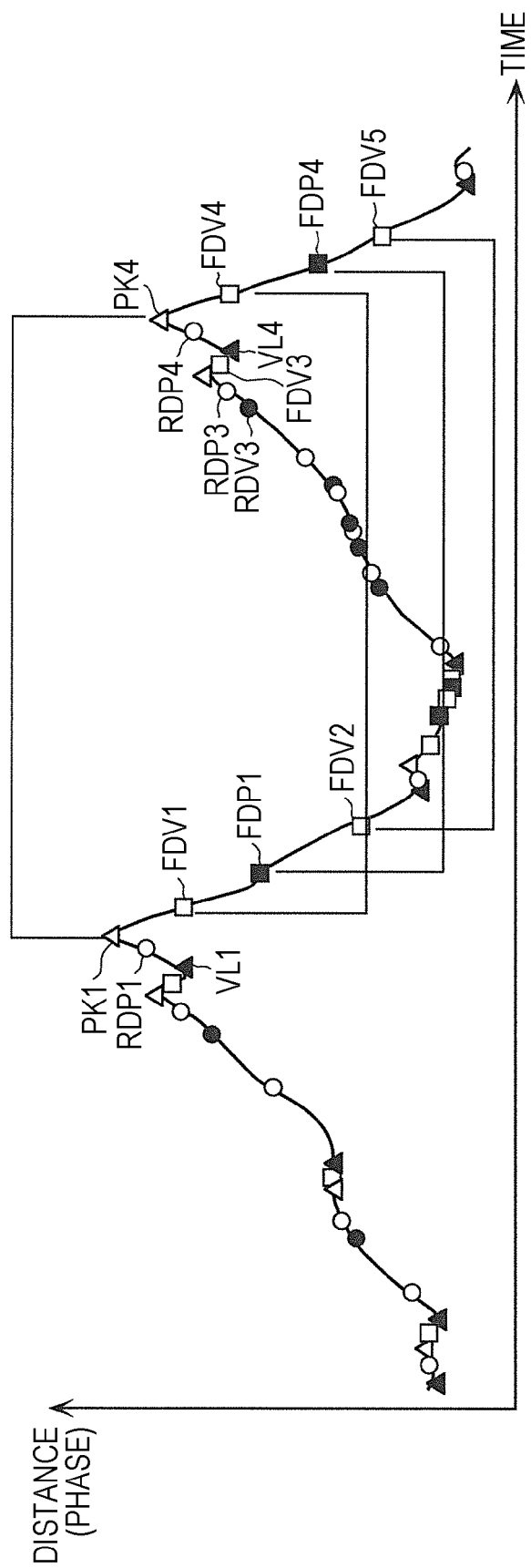
FIG. 19 is a graph illustrating characteristic points of a second heartbeat corresponding to characteristic points of a first heartbeat, calculated for the respective characteristic points of the first heartbeat according to the second embodiment.

FIG. 19 illustrates the characteristic points of the second heartbeat corresponding to the characteristic points of the first heartbeat, each of the characteristic points of the second heartbeat being determined for a corresponding one of the characteristic points of the first heartbeat. The characteristic point PK4 is determined as the characteristic point of the second heartbeat corresponding to the characteristic point PK1 of the first heartbeat, the characteristic point FDV4 is determined as the characteristic point of the second heartbeat corresponding to the characteristic point FDV1 of the first heartbeat, and the characteristic point FDP4 is determined as the characteristic point of the second heartbeat corresponding to the characteristic point FDP1 of the first heartbeat. In this way, for each characteristic point of the first heartbeat (reference point), the characteristic point corresponding to the reference point is determined as a corresponding characteristic point.

Furthermore, the output unit 108 calculates an interval which is a difference in time between a characteristic point as a reference point and a characteristic point corresponding to the reference point (corresponding characteristic point), as a heartbeat interval in an average time of the characteristic points.

Figure 20:
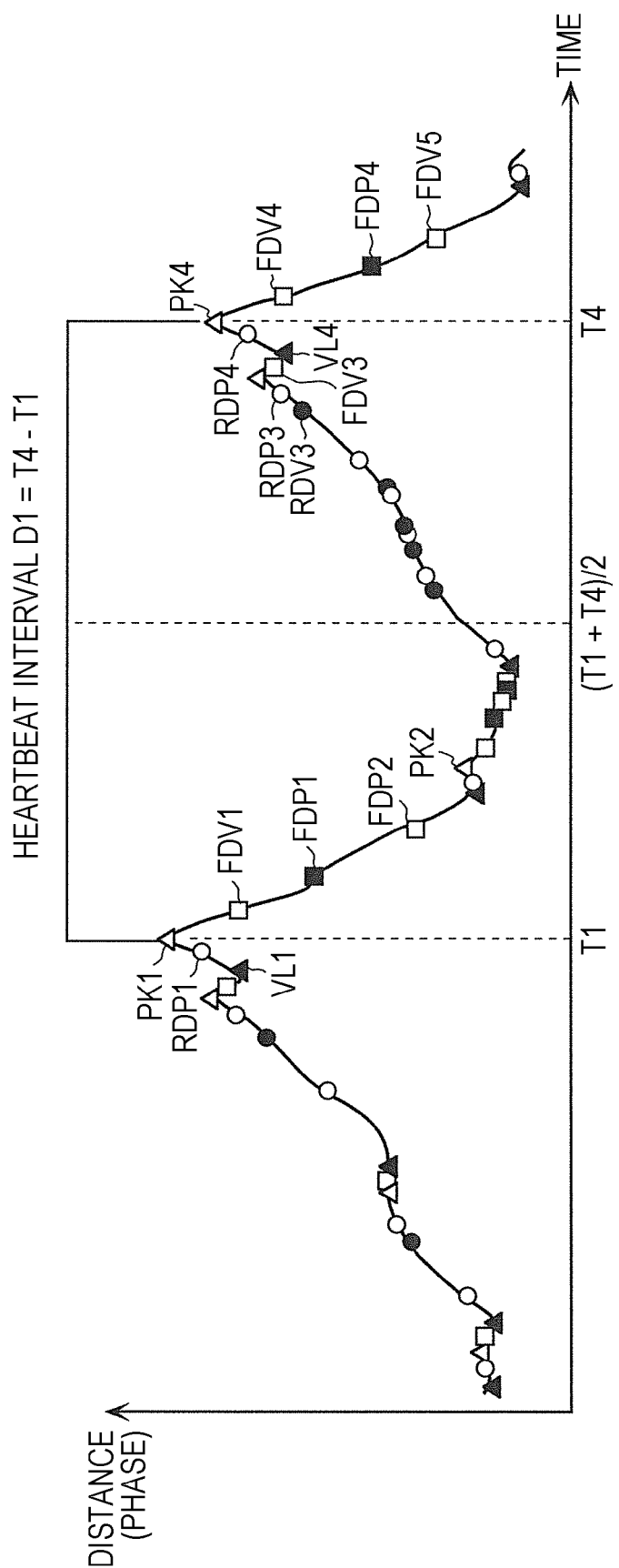
FIG. 20 is a graph for describing calculation of an average time and a heartbeat interval according to the second embodiment.

FIG. 20 is a graph for describing calculation of an average time and heartbeat interval for the characteristic points PK1 and PK4. The time of the characteristic point PK1 as a reference point is represented by T1 and the time of the characteristic point PK4 as a corresponding characteristic point is represented by T4. The output unit 108 calculates an average time for these characteristic points by dividing (T1+T4) by 2 and also calculates a heartbeat interval D1 in the average time by subtracting T1 from T4.

Figure 21:
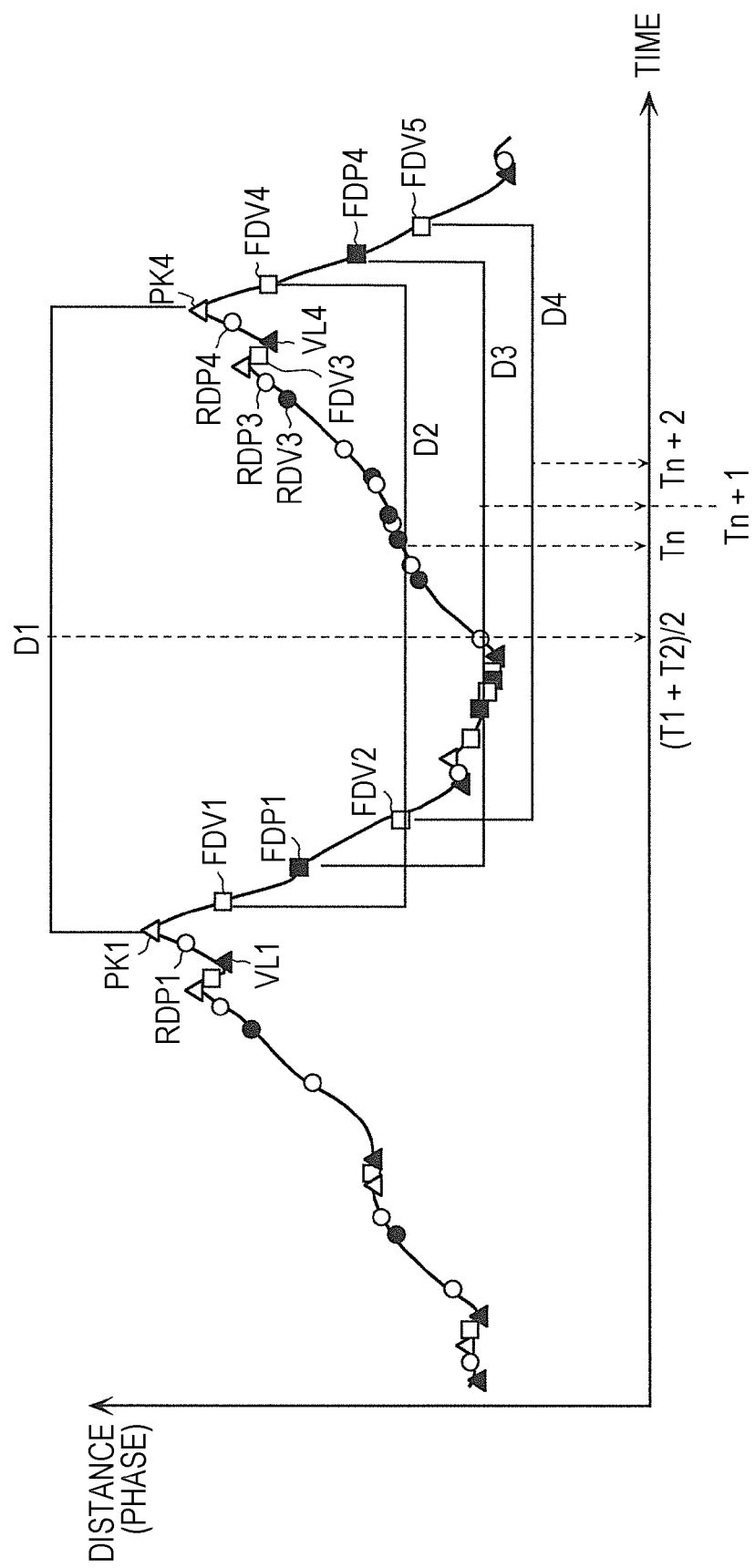
FIG. 21 is a graph for describing calculation of average times and heartbeat intervals for individual characteristic points according to the second embodiment.

FIG. 21 is a graph for describing calculation of an average time and heartbeat interval for each characteristic point. As described above, the characteristic points corresponding to the characteristic points FDV1, FDP1, and so forth are determined in addition to the characteristic point PK1. Specifically, the characteristic point FDV4 corresponding to the characteristic point FDV1 is determined, and the characteristic point FDP4 corresponding to the characteristic point FDP1 is determined. The output unit 108 calculates an average time Tn for the characteristic points FDV1 and FDV4 and calculates an average time Tn+1 for the characteristic points FDP1 and FDP4. Also, the output unit 108 calculates a heartbeat interval D2 in the average time Tn and calculates a heartbeat interval D3 in the average time Tn+1. In this way, the output unit 108 calculates a heartbeat interval for each set of characteristic points corresponding to each other.

Figure 22:
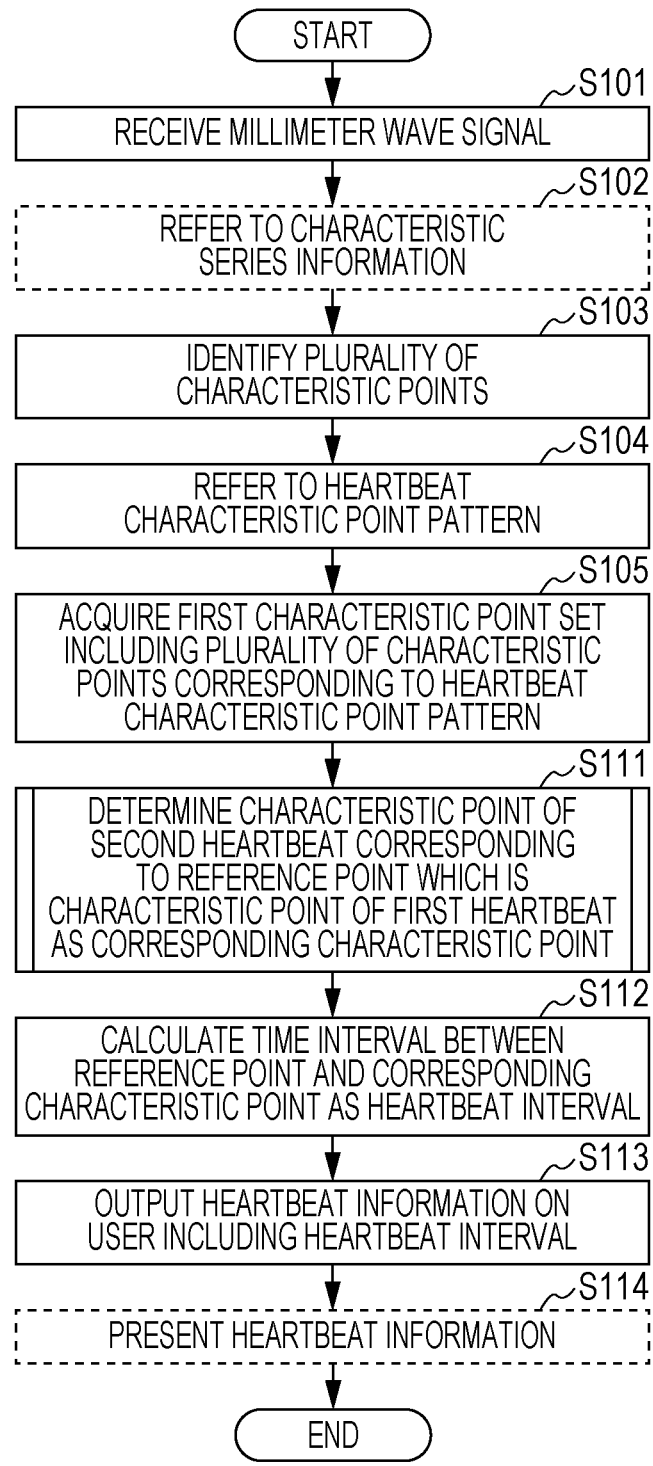
FIG. 22 is a flowchart of a process performed by the heartbeat measuring apparatus according to the second embodiment.

FIG. 22 is a flowchart of a process performed by the heartbeat measuring apparatus 111 according to the second embodiment.

The heartbeat measuring apparatus 111 performs steps S101 to S105 in the same manner as the heartbeat measuring apparatus 110 according to the first embodiment.

Subsequently, in step S111, the output unit 108 determines a corresponding characteristic point that corresponds to a reference point, which is a characteristic point of the heartbeat for the first characteristic point set (first heartbeat), and that is a characteristic point of a heartbeat different from the first heartbeat (second heartbeat). In step S112, the output unit 108 calculates a time difference (time interval), which is a difference between the time of the reference point and the time of the corresponding characteristic point, as a heartbeat interval. In step S113, the output unit 108 outputs heartbeat information on the user further including the heartbeat interval.

In step S114, the presentation unit 107 presents the heartbeat information on the user output from the output unit 108.

Figure 23:
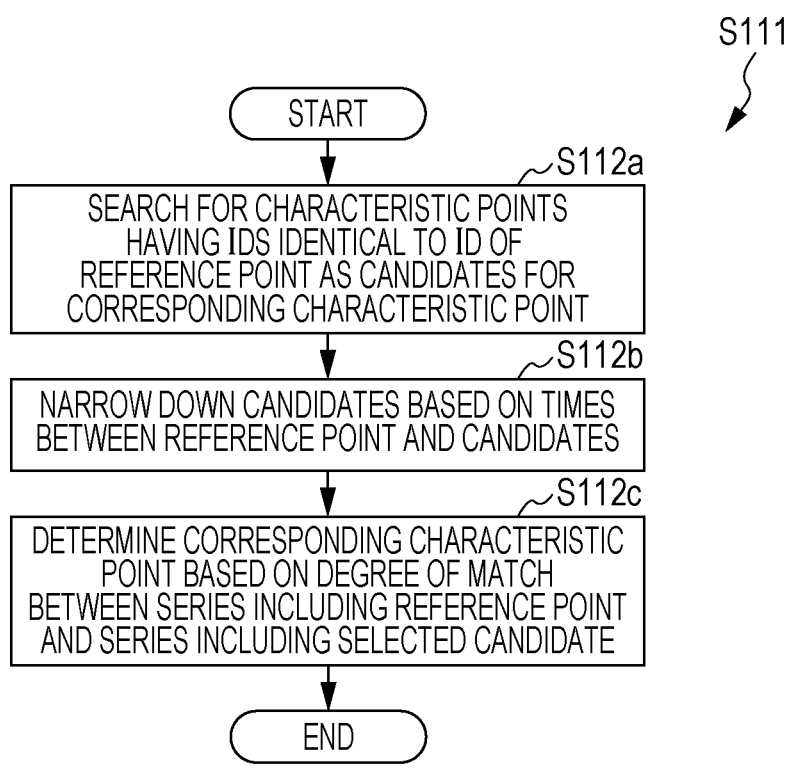
FIG. 23 is a flowchart illustrating the details of part of the process performed by the heartbeat measuring apparatus according to the second embodiment.

FIG. 23 is a flowchart illustrating the details of step S111 in FIG. 22.

In step S112a, the output unit 108 searches for, as candidates for the corresponding characteristic point, characteristic points having IDs that match the ID of the reference point. In step S112b, the output unit 108 narrows down the candidates, based on the times between the reference point and the respective candidates. In step S112c, the output unit 108 determines the corresponding characteristic point, based on the degree of match between a series including the reference point and a series including a candidate resulting from the narrowing down.

As described above, a heartbeat interval is calculated for each characteristic point, regardless of a peak, in the second embodiment. If a peak is used in heartbeat data corresponding to heartbeats, it may be impossible to accurately detect heartbeat intervals due to noise or a measurement situation. In the second embodiment, a heartbeat interval is detected for each characteristic point in consideration of the similarity in the shape of heartbeat data between heartbeats, and accordingly heartbeat intervals can be measured more robustly and more accurately.

Modification Example

In the second embodiment, the certain threshold is used for determining a characteristic point corresponding to a characteristic point of the first heartbeat. The certain threshold represents a time based on the characteristic point of the first heartbeat. Instead of such a threshold, a correlation value based on a signal intensity of a waveform including the characteristic point of the first heartbeat may be used. In the modification example, a characteristic point of the second heartbeat corresponding to a characteristic point of the first heartbeat (corresponding characteristic point) is determined by using the correlation value.

Figure 24:
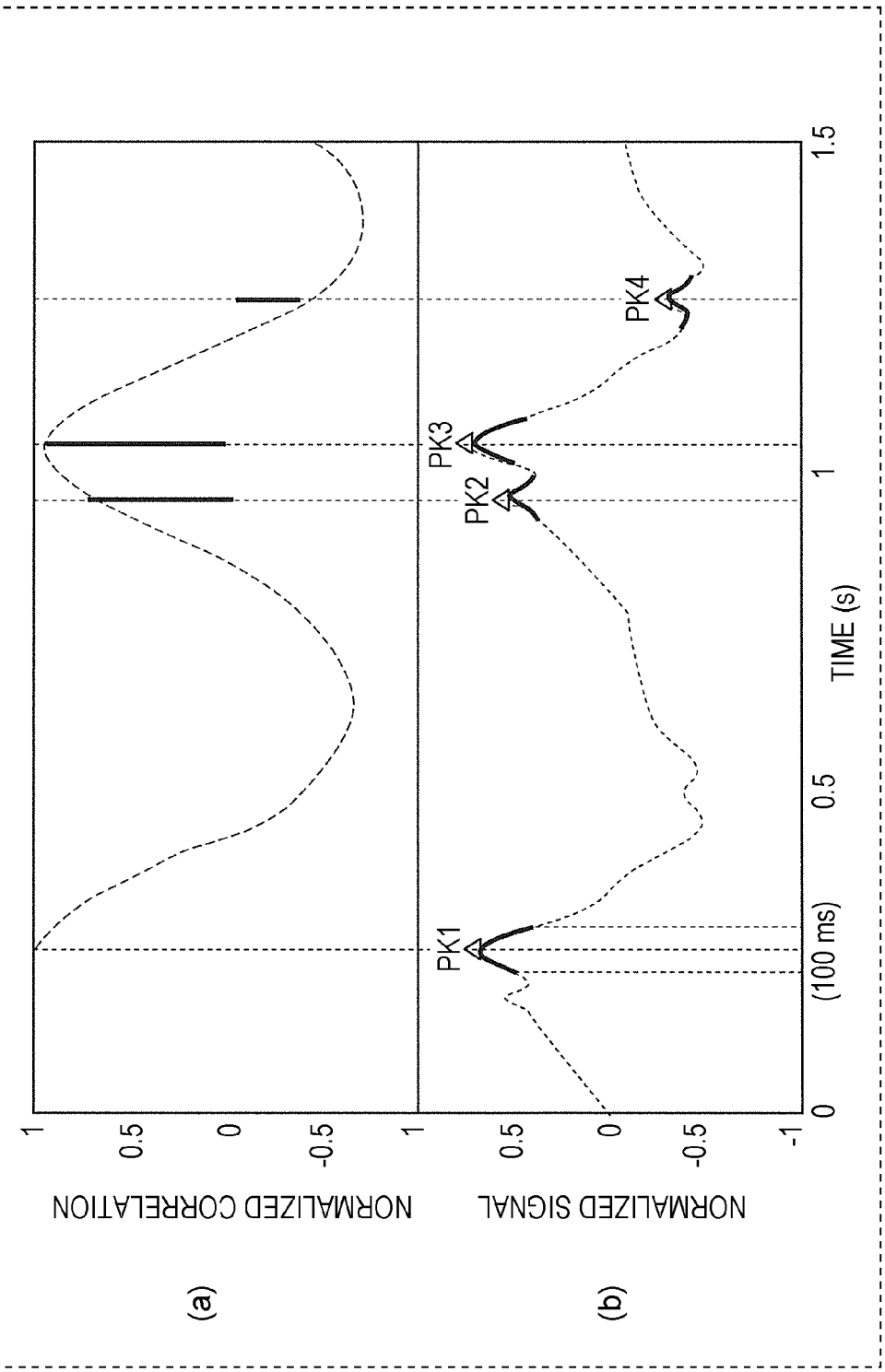
FIG. 24 is a graph for describing calculation of a corresponding characteristic point using a correlation value according to a modification example of the second embodiment.

FIG. 24 is a graph for describing calculation of a corresponding characteristic point using a correlation value. The graph with a broken line illustrated in FIG. 24(b) represents heartbeat data.

The output unit 108 searches for, among a plurality of characteristic points that have been identified, a plurality of characteristic points whose types are identical to the type of a reference point which is a characteristic point of the heartbeat for the first characteristic point set. Specifically, the output unit 108 searches for, as candidates for a corresponding reference point, characteristic points whose IDs are identical to the ID of the reference point, as in step S112a of FIG. 23.

Subsequently, the output unit 108 determines the corresponding characteristic point, based on the signal intensity at the reference point and the signal intensities at the plurality of characteristic points obtained through the search (the candidates). Specifically, the output unit 108 determines, based on the signal intensities, the corresponding characteristic point that corresponds to the reference point and that is included in the characteristic points of a heartbeat different from the heartbeat for the first characteristic point set among the plurality of characteristic points obtained through the search. If the heartbeat for the first characteristic point set is the first heartbeat, the heartbeat different from the heartbeat for the first characteristic point set is the second heartbeat. The signal intensity is not necessarily a signal intensity at a characteristic point, and may be a signal intensity of a waveform of a portion of the millimeter wave signal including the characteristic point. That is, the output unit 108 determines the corresponding characteristic point, based on the correlation value between the signal intensity of the waveform of the portion of the millimeter wave signal including the reference point which is a characteristic point of the heartbeat for the first characteristic point set and the signal intensities of the waveforms of the portions of the millimeter wave signal including the individual characteristic points obtained through the search.

Specifically, as illustrated in FIG. 24, the output unit 108 calculates correlation values between heartbeat data for a certain time period including before and after the time of the characteristic point PK1 as a reference point, and heartbeat data for a certain time period including before and after the time of each of the characteristic points PK2 to PK4 as candidates. The certain time period is, for example, 100 ms. The heartbeat data for the time period around the time of each characteristic point including the characteristic point PK1 is represented by a bold solid line in FIG. 24(b). The graph with a broken line illustrated in FIG. 24(a) represents correlation values between the heartbeat data for the time period around the time of the characteristic point PK1 and pieces of heartbeat data for the time periods around the respective times. The time period around the time is the above-described certain time period including before and after the time.

As illustrated in FIG. 24(a), the correlation value at the time of the characteristic point PK1 is high of 1, and the correlation value decreases as the time elapses. The correlation value between the heartbeat data for 100 ms including before and after the time of the characteristic point PK1 and the heartbeat data for 100 ms including before and after the time of the characteristic point PK2 is 0.8. The correlation value between the heartbeat data for 100 ms including before and after the time of the characteristic point PK1 and the heartbeat data for 100 ms including before and after the time of the characteristic point PK3 is about 1, which is very high. The correlation value between the heartbeat data for 100 ms including before and after the time of the characteristic point PK1 and the heartbeat data for 100 ms including before and after the time of the characteristic point PK4 is −0.3. Thus, among the candidates, the heartbeat data at the characteristic point PK3 has the highest correlation value. This is because the shape of the heartbeat data for 100 ms including before and after the time of the characteristic point PK3 is the most similar to the shape of the heartbeat data for 100 ms including before and after the time of the characteristic point PK1. The shape of the heartbeat data is a shape including a signal intensity. As a result, the output unit 108 determines the characteristic point PK3 to be the corresponding characteristic point.

The output unit 108 outputs heartbeat information on the user further including a time difference which is a difference between the time of the characteristic point PK1 as a reference point and the time of the characteristic point PK3 as a corresponding characteristic point.

As described above, in the modification example, correlation values between the heartbeat data for a characteristic point as a reference point and the heartbeat data for each of candidate characteristic points are calculated, and thereby the characteristic point corresponding to the reference point (corresponding characteristic point) is determined. In the modification example, correlation values for the times of individual candidate characteristic points are calculated, without correlation values for all the times in the heartbeat data being calculated, and accordingly the amount of calculation is reduced.

Figure 25:
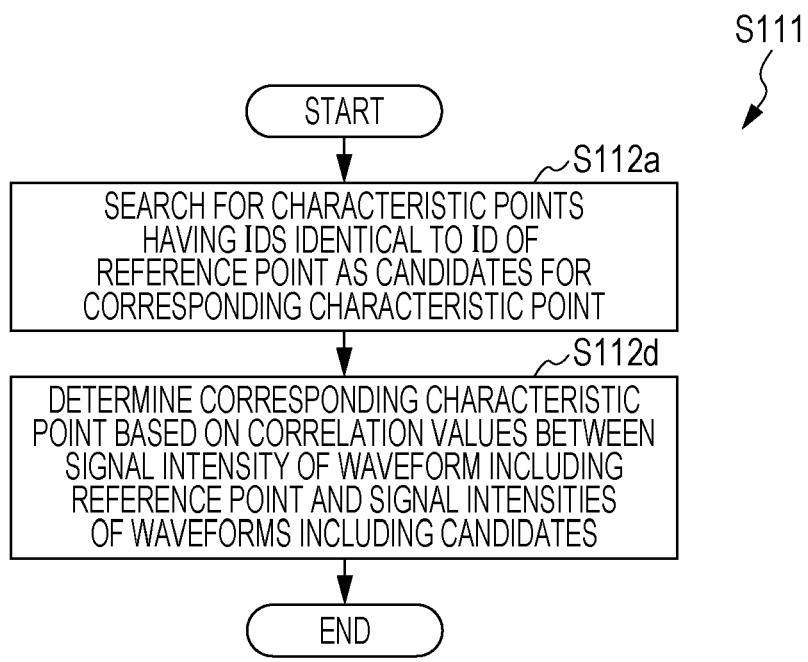
FIG. 25 is a flowchart illustrating the details of part of the process according to the modification example of the second embodiment.

FIG. 25 is a flowchart illustrating the details of step S111 according to the modification example of the second embodiment.

In step S112a, the output unit 108 searches for, as candidates for the corresponding characteristic point, characteristic points having IDs that match the ID of the reference point. In step S112d, the output unit 108 determines the corresponding characteristic point, based on correlation values between the signal intensity of a waveform including the reference point and the signal intensities of waveforms including the respective candidates. The output unit 108 determines the corresponding characteristic point that corresponds to the reference point and that is included in the characteristic points of a heartbeat different from the heartbeat for the first characteristic point set among the plurality of characteristic points (candidates) obtained through the search, based on the calculated correlation values.

As described above, in the modification example, the output unit 108 searches for, among a plurality of characteristic points that have been identified, a plurality of characteristic points whose types are identical to the type of a reference point, which is a characteristic point of the heartbeat for the first characteristic point set. Subsequently, the output unit 108 determines a corresponding characteristic point, based on the signal intensity at the reference point and the signal intensities at the plurality of characteristic points obtained through the search. That is, the output unit 108 determines, based on the signal intensities, a corresponding characteristic point that corresponds to the reference point and that is included in the characteristic points of a heartbeat different from the heartbeat for the first characteristic point set among the plurality of characteristic points obtained through the search. Subsequently, the output unit 108 outputs heartbeat information on the user further including a time difference which is a difference between the time of the reference point and the time of the corresponding characteristic point.

Accordingly, heartbeat intervals as the above-described time differences can be correctly measured for a plurality of characteristic points of the heartbeat for the first characteristic point set. Furthermore, since a plurality of characteristic points whose types are identical to the type of the reference point are searched for and then the corresponding characteristic point is determined based on the signal intensities at the characteristic points, it is not necessary to determine the corresponding characteristic point in consideration of the signal intensities at the characteristic points whose types are different from the type of the reference point, and accordingly the amount of calculation can be reduced.

The embodiments and modification example of the present disclosure related to a heartbeat measuring apparatus have been described above. The present disclosure is not limited to the embodiments and modification example. Various modifications of the above-described embodiments and modification example and any combination of elements in different embodiments that are conceived of by a person skilled in the art may be included in the present disclosure without deviating from the gist of the present disclosure.

In the modification example of the second embodiment, signal intensities are used for determining a corresponding characteristic point. Signal intensities may be used for acquiring a characteristic point set of the second heartbeat (second characteristic point set). That is, the acquisition unit 105 acquires a first characteristic point set as the first heartbeat and then searches for a plurality of characteristic points whose types are identical to the type of a reference point which is a characteristic point of the first heartbeat. Subsequently, as in the above-described modification example, the acquisition unit 105 determines a corresponding characteristic point, based on the signal intensity of the reference point and the signal intensities of the plurality of characteristic points obtained through the search. For example, the acquisition unit 105 determines the characteristic point corresponding to the characteristic point PK1, based on the characteristic point PK1 as a reference point and the plurality of characteristic points PK2, PK3, and PK4 obtained through the search. As a result, the acquisition unit 105 determines the characteristic points PK2 and PK3 as a plurality of corresponding characteristic points. In this case, the acquisition unit 105 performs pattern matching between each of series of characteristic points respectively including the characteristic points PK2 and PK3 as corresponding characteristic points and the characteristic points therearound, and a series indicated by a heartbeat characteristic point pattern stored in the memory 104. As a result, the acquisition unit 105 acquires, as a second characteristic point set, the series of characteristic points including the characteristic point PK3 and the characteristic points therearound. Pattern matching may be performed in this way on the corresponding characteristic point and the characteristic points therearound, and thus the amount of calculation can be reduced.

In the present disclosure, the above-described computer program or digital signals may be transmitted through an electric communication line, a wireless or wired line, or a network such as the Internet.

In the present disclosure, all or some of the units and devices, or all or some of the functional blocks illustrated in the block diagrams in FIGS. 2 and 17 may be implemented by one or more electronic circuits including a semiconductor device, a semiconductor integrated circuit (IC), or a large scale integration (LSI). The LSI or IC may be integrated on one chip or may be configured by combining a plurality of chips. For example, the functional blocks other than storage elements may be integrated on one chip. Here, the terms LSI and IC are used, but they may be called a system LSI, very large scale integration (VLSI), or ultra large scale integration (ULSI) in accordance with the degree of integration. A field programmable gate array (FPGA), which is programmed after the manufacturing of the LSI, or a reconfigurable logic device, in which the connection relationship among the elements in the LSI can be reconfigured or the circuit section in the LSI can be set up, may be used for the same purpose.

Furthermore, all or some of the functions or operations of a unit, device, or part of the device may be executed by software processing. In this case, the software is recorded on a non-transitory recording medium, such as one or more read only memories (ROMs), optical discs, or hard disk drives. When the software is executed by a processor, the software causes a peripheral device to execute a specific function of the software. A system or device may include one or more non-transitory recording media on which the software is recorded, a processor, and a necessary hardware device, such as an interface.

The apparatus according to the present disclosure may be a computer system including a microprocessor and a memory, the memory may store the foregoing computer program, and the microprocessor may executed the computer program.

The foregoing program or digital signals may be transferred by recording it on the recording medium, or the foregoing program or digital signals may be transferred through the network, so as to execute or process the program or digital signals in another independent computer system.

In the above-described embodiments, the individual elements may be constituted by dedicated hardware or may be implemented by executing a software program suitable for the elements. The individual elements may be implemented when a program execution unit such as a CPU or processor reads and executes a software program recorded on a recording medium such as a hard disk or semiconductor memory. The software that implements the heartbeat measuring apparatus according to the above-described embodiments is the following program.

The program is a computer program executed by a computer, the computer program causing the computer to execute a process including (a) receiving a millimeter wave signal reflected by a user; (b) identifying a plurality of characteristic points of the received millimeter wave signal in time series, the plurality of characteristic points including a local maximum point, a local minimum point, and an inflection point defined by information representing a positive or negative sign of a slope of the millimeter wave signal and information representing a positive or negative sign of a third-order derivative of the millimeter wave signal; (c) acquiring, from among the plurality of characteristic points that have been identified, a first characteristic point set including first characteristic points that are arranged in an order identical to a first arrangement order, with reference to a heartbeat characteristic point pattern stored in a memory, the heartbeat characteristic point pattern indicating the first arrangement order of a first inflection point following a first local maximum point and having a negative slope and a positive third-order derivative, a first local minimum point following the first inflection point, a second inflection point following the first local minimum point and having a positive slope and a negative third-order derivative, and a second local maximum point following the second inflection point; and (d) outputting heartbeat information on the user including a time based on the first characteristic points included in the first characteristic point set that has been acquired.

Any combination of the above-described embodiments and the modification example may be accepted.

The embodiments disclosed herein are examples from every point of view and should be considered as nonrestrictive. The scope of the present disclosure is defined by the following claims, not the description given above, and includes all changes within the meaning and scope equivalent to those of the claims.

The present disclosure is applicable to, in particular, a heartbeat measuring apparatus or the like.

What is claimed is:

1. A heartbeat measuring apparatus comprising:
a receiver that receives a millimeter wave signal reflected by a user;
an identifier that identifies a plurality of characteristic points of the received millimeter wave signal in time series, the plurality of characteristic points including a local maximum point, a local minimum point, and an inflection point defined by information representing a positive or negative sign of a slope of the millimeter wave signal and information representing a positive or negative sign of a third-order derivative of the millimeter wave signal;
a memory that stores a heartbeat characteristic point pattern indicating a first arrangement order of a first inflection point following a first local maximum point and having a negative slope and a positive third-order derivative, a first local minimum point following the first inflection point, a second inflection point following the first local minimum point and having a positive slope and a negative third-order derivative, and a second local maximum point following the second inflection point;
an acquirer that acquires, from among the plurality of characteristic points that have been identified, a first characteristic point set including first characteristic points that are arranged in an order identical to the first arrangement order; and
an outputter that outputs heartbeat information on the user including a time based on the first characteristic points included in the first characteristic point set that has been acquired.

2. The heartbeat measuring apparatus according to claim 1, wherein
the acquirer further acquires, from among the plurality of characteristic points that have been identified, a second characteristic point set including second characteristic points different from the first characteristic points included in the first characteristic point set, the second characteristic points being arranged in an order identical to the first arrangement order, and
the outputter outputs the heartbeat information on the user further including a time difference which is a difference between a time based on the first characteristic points included in the first characteristic point set and a time based on the second characteristic points included in the second characteristic point set.

3. The heartbeat measuring apparatus according to claim 1, wherein
the outputter searches for, among the plurality of characteristic points that have been identified except the first characteristic points included in the first characteristic point set, a plurality of characteristic points whose types are identical to a type of a reference point, the reference point being one of the first characteristic points included in the first characteristic point set,
the outputter determines, based on an intensity of the millimeter wave signal at the reference point and intensities of the millimeter wave signal at the plurality of characteristic points obtained through the search, a corresponding characteristic point that corresponds to the reference point and that is included in a characteristic point set of a heartbeat different from a heartbeat for the first characteristic point set among the plurality of characteristic points whose types are identical to the type of the reference point,
the outputter outputs the heartbeat information on the user further including a time difference which is a difference between a time of the reference point and a time of the corresponding characteristic point, and
the type of each of the plurality of characteristic points is one of a local maximum point, a local minimum point, an inflection point having a negative slope and a positive third-order derivative, an inflection point having a negative slope and a negative third-order derivative, an inflection point having a positive slope and a positive third-order derivative, and an inflection point having a positive slope and a negative third-order derivative.

4. The heartbeat measuring apparatus according to claim 2, wherein the time difference is any one of
a difference between a time of a first local maximum point included in the first characteristic point set and a time of a first local maximum point included in the second characteristic point set,
a difference between a time of a first inflection point included in the first characteristic point set and a time of a first inflection point included in the second characteristic point set,
a difference between a time of a local minimum point included in the first characteristic point set and a time of a local minimum point included in the second characteristic point set,
a difference between a time of a second inflection point included in the first characteristic point set and a time of a second inflection point included in the second characteristic point set, and
a difference between a time of a second local maximum point included in the first characteristic point set and a time of a second local maximum point included in the second characteristic point set.

5. A heartbeat measuring method comprising:
receiving a millimeter wave signal reflected by a user;
identifying a plurality of characteristic points of the received millimeter wave signal in time series, the plurality of characteristic points including a local maximum point, a local minimum point, and an inflection point defined by information representing a positive or negative sign of a slope of the millimeter wave signal and information representing a positive or negative sign of a third-order derivative of the millimeter wave signal;
acquiring, from among the plurality of characteristic points that have been identified, a first characteristic point set including first characteristic points that are arranged in an order identical to a first arrangement order, with reference to a heartbeat characteristic point pattern stored in a memory, the heartbeat characteristic point pattern indicating the first arrangement order of a first inflection point following a first local maximum point and having a negative slope and a positive third-order derivative, a first local minimum point following the first inflection point, a second inflection point following the first local minimum point and having a positive slope and a negative third-order derivative, and a second local maximum point following the second inflection point; and outputting heartbeat information on the user including a time based on the first characteristic points included in the first characteristic point set that has been acquired.

6. The heartbeat measuring method according to claim 5, wherein the acquiring includes acquiring, from among the plurality of characteristic points that have been identified, a second characteristic point set including second characteristic points different from the first characteristic points included in the first characteristic point set, the second characteristic points being arranged in an order identical to the first arrangement order, and the outputting includes outputting the heartbeat information on the user further including a time difference which is a difference between a time based on the first characteristic points included in the first characteristic point set and a time based on the second characteristic points included in the second characteristic point set.

7. The heartbeat measuring method according to claim 5, wherein the outputting includes searching for, among the plurality of characteristic points that have been identified except the first characteristic points included in the first characteristic point set, a plurality of characteristic points whose types are identical to a type of a reference point, the reference point being one of the first characteristic points included in the first characteristic point set, the outputting includes determining, based on an intensity of the millimeter wave signal at the reference point and intensities of the millimeter wave signal at the plurality of characteristic points obtained through the search, a corresponding characteristic point that corresponds to the reference point and that is included in a characteristic point set of a heartbeat different from a heartbeat for the first characteristic point set among the plurality of characteristic points whose types are identical to the type of the reference point, the outputting includes outputting the heartbeat information on the user further including a time difference which is a difference between a time of the reference point and a time of the corresponding characteristic point, and the type of each of the plurality of characteristic points is one of a local maximum point, a local minimum point, an inflection point having a negative slope and a positive third-order derivative, an inflection point having a negative slope and a negative third-order derivative, an inflection point having a positive slope and a positive third-order derivative, and an inflection point having a positive slope and a negative third-order derivative.

8. The heartbeat measuring method according to claim 6, wherein the time difference is any one of a difference between a time of a first local maximum point included in the first characteristic point set and a time of a first local maximum point included in the second characteristic point set, a difference between a time of a first inflection point included in the first characteristic point set and a time of a first inflection point included in the second characteristic point set, a difference between a time of a local minimum point included in the first characteristic point set and a time of a local minimum point included in the second characteristic point set, a difference between a time of a second inflection point included in the first characteristic point set and a time of a second inflection point included in the second characteristic point set, and a difference between a time of a second local maximum point included in the first characteristic point set and a time of a second local maximum point included in the second characteristic point set.

9. A non-transitory computer-readable recording medium storing therein a control program for causing a heartbeat measuring apparatus including a processor to execute a process, the process comprising:

receiving a millimeter wave signal reflected by a user;

identifying a plurality of characteristic points of the received millimeter wave signal in time series, the plurality of characteristic points including a local maximum point, a local minimum point, and an inflection point defined by information representing a positive or negative sign of a slope of the millimeter wave signal and information representing a positive or negative sign of a third-order derivative of the millimeter wave signal;

acquiring, from among the plurality of characteristic points that have been identified, a first characteristic point set including first characteristic points that are arranged in an order identical to a first arrangement order, with reference to a heartbeat characteristic point pattern stored in a memory, the heartbeat characteristic point pattern indicating the first arrangement order of a first inflection point following a first local maximum point and having a negative slope and a positive third-order derivative, a first local minimum point following the first inflection point, a second inflection point following the first local minimum point and having a positive slope and a negative third-order derivative, and a second local maximum point following the second inflection point; and outputting heartbeat information on the user including a time based on the first characteristic points included in the first characteristic point set that has been acquired.

10. The non-transitory computer-readable recording medium according to claim 9, wherein the acquiring includes acquiring, from among the plurality of characteristic points that have been identified, a second characteristic point set including second characteristic points different from the first characteristic points included in the first characteristic point set, the second characteristic points being arranged in an order identical to the first arrangement order, and the outputting includes outputting the heartbeat information on the user further including a time difference which is a difference between a time based on the first characteristic points included in the first characteristic point set and a time based on the second characteristic points included in the second characteristic point set.

11. The non-transitory computer-readable recording medium according to claim 9, wherein
- the outputting includes searching for, among the plurality of characteristic points that have been identified except the first characteristic points included in the first characteristic point set, a plurality of characteristic points whose types are identical to a type of a reference point, the reference point being one of the first characteristic points included in the first characteristic point set,
- the outputting includes determining, based on an intensity of the millimeter wave signal at the reference point and intensities of the millimeter wave signal at the plurality of characteristic points obtained through the search, a corresponding characteristic point that corresponds to the reference point and that is included in a characteristic point set of a heartbeat different from a heartbeat for the first characteristic point set among the plurality of characteristic points whose types are identical to the type of the reference point,
- the outputting includes outputting the heartbeat information on the user further including a time difference which is a difference between a time of the reference point and a time of the corresponding characteristic point, and
- the type of each of the plurality of characteristic points is one of a local maximum point, a local minimum point, an inflection point having a negative slope and a positive third-order derivative, an inflection point having a negative slope and a negative third-order derivative, an inflection point having a positive slope and a positive third-order derivative, and an inflection point having a positive slope and a negative third-order derivative.

* * * * *